US008357692B2

(12) United States Patent
Teitelbaum et al.

(10) Patent No.: US 8,357,692 B2
(45) Date of Patent: Jan. 22, 2013

(54) METHODS OF TREATMENT OF BONE DEGENERATIVE DISEASES

(75) Inventors: Steven L. Teitelbaum, St. Louis, MO (US); Carl J. DeSelm, St. Louis, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 13/162,960

(22) Filed: Jun. 17, 2011

(65) Prior Publication Data

US 2011/0311519 A1 Dec. 22, 2011

Related U.S. Application Data

(60) Provisional application No. 61/356,637, filed on Jun. 20, 2010.

(51) Int. Cl.
*A61K 31/517* (2006.01)
*A61K 38/00* (2006.01)
*A61P 19/10* (2006.01)

(52) U.S. Cl. ................... 514/266.22; 514/16.9; 514/306; 514/266.21; 514/230.5; 514/269; 514/309; 424/130.1

(58) Field of Classification Search .............. 514/266.22, 514/266.21, 230.5, 16.9, 315, 263, 309, 306, 514/259; 424/130.1
See application file for complete search history.

(56) References Cited

U.S. PATENT DOCUMENTS

| | | | |
|---|---|---|---|
| 2,694,711 A | 11/1954 | Baker et al. | |
| 3,320,124 A | 5/1967 | Waletsky et al. | |
| 4,632,926 A | 12/1986 | Giarda et al. | |
| RE39,574 E | 4/2007 | Pines et al. | |
| 7,438,910 B2 | 10/2008 | Varnum et al. | |
| 7,638,480 B2 | 12/2009 | Power et al. | |
| 7,713,994 B2 | 5/2010 | Tsou et al. | |
| 2002/0045213 A1 | 4/2002 | Jing | |
| 2003/0017151 A1 | 1/2003 | Dougall et al. | |
| 2009/0117126 A1 | 5/2009 | Adams et al. | |
| 2009/0123389 A1 | 5/2009 | Whitman et al. | |
| 2010/0029615 A1 | 2/2010 | Munchhof et al. | |

OTHER PUBLICATIONS

Bruck et al., "Halofuginone to prevent and treat thioacetamide-induced liver fibrosis in rats," Hepatology, 33(2), 379-386, 2001.
Choi et al., "Halofuginone, a specific collagen type I inhibitor, reduces anastomotic intimal hyperplasia," Arch. Surg., 130(3), 257-261, 1995.
Gaffen, S.L., "Biology of recently discovered cytokines: interleukin-17—a unique inflammatory cytokine with roles in bone biology and arthritis," Arthritis Res. & Therapy 6: 240-247, 2004.
Galic et al., "Adipose tissue as an endocrine organ," Mol. Cell Endocrinol., 316(2), 129-139, 2010.
Goswami, J., et al., "A bone-protective role for IL-17 receptor signaling in ovariectomy-induced bone loss," Eur. J. Immunol. 39: 2831-9, 2009.
Granot et al., "Halofuginone: an inhibitor of collagen type I synthesis," Biochim Biophys Acta, 1156(2), 107-112, 1993.

(Continued)

*Primary Examiner* — Savitha Rao
(74) *Attorney, Agent, or Firm* — Zackson Law LLC; Saul L. Zackson

(57) ABSTRACT

Methods of reducing bone loss and treating degenerative bone diseases such as osteoporosis are disclosed. The methods comprise administration of an agent that inhibits signaling through the IL-17 pathway, such as an antibody or a quinazolinone analogue such as halofuginone.

3 Claims, 20 Drawing Sheets

OTHER PUBLICATIONS

Halevy et al., "Inhibition of collagen type I synthesis by skin fibroblasts of graft versus host disease and scleroderma patients: effect of halofuginone," Biochem. Pharmacol., 52(7), 1057-1063, 1996.

Kikuchi, H., et al. "Potent antimalarial febrifugine analogues against the plasmodium malaria parasite," J. Med. Chem. 45, 2563-2570, 2002.

Levi-Schaffer et al., "Inhibition of collagen synthesis and changes in skin morphology in murine graft-versus-host disease and tight skin mice: effect of halofuginone," J. Invest. Dermatol., 106(1), 84-88, 1996.

Liu et al., "Leptin increases in Vogt-Koyanagi-Harada (VKH) disease and promotes cell proliferation and inflammatory cytokine secretion," Br. J. Ophthalmol., 92(4), 557-561, 2008.

McGaha et al., "Halofuginone, an inhibitor of type-I collagen synthesis and skin sclerosis, blocks transforming-growth-factor-beta-mediated Smad3 activation in fibroblasts," J. Invest. Dermatol., 118(3), 461-470, 2002.

McLaughlin, N.P., et al., "Dihydroxylation of vinyl sulfones: stereoselective synthesis of (+)- and (−)-febrifugine and halofuginone," J. Org. Chem. 2010 75: 518-521, 2010.

Nagler et al., "Halofuginone—an inhibitor of collagen type I synthesis—prevents postoperative formation of abdominal adhesions," Ann. Surg., 227(4), 575-582, 1998.

Nagler et al., "Reduction in pulmonary fibrosis in vivo by halofuginone," Am. J. Respir. Crit. Care Med., 154(4 Pt 1), 1082-1086, 1996.

Pines et al., "Halofuginone to treat fibrosis in chronic graft-versus-host disease and scleroderma," Biol. Blood Marrow Transplant, 9(7), 417-425, 2003.

Pines et al., "Halofuginone, a specific inhibitor of collagen type I synthesis, prevents dimethylnitrosamine-induced liver cirrhosis," J. Hepatol., 27(2), 391-398 1997.

Pines et al., "Reduction in dermal fibrosis in the tight-skin (Tsk) mouse after local application of halofuginone," Biochem. Pharmacol., 62(9), 1221-1227, 2001.

Shin et al., "Interleukin-17A inhibits adipocyte differentiation in human mesenchymal stem cells and regulates pro-inflammatory responses in adipocytes," Biochem. Pharmacol., 77(12), 1835-1844, 2009.

Sumarac-Dumanovic et al., "Increased activity of interleukin-23/interleukin-17 proinflammatory axis in obese women," Int. J. Obes. (Lond), 33(1), 151-156, 2009.

Sundrud, M.S., et al., "Halofuginone inhibits TH17 cell differentiation by activating the amino acid starvation response," Science 324: 1334-1338, 2009.

Takaya, Y. et al., "New type of febrifugine analogues, bearing a quinolizidine moiety, show potent antimalarial activity against *Plasmodium malaria* parasite," J. Med. Chem 42: 3163-3166, 1999.

Udagawa, N., et al., "The molecular mechanism of osteoclastogenesis in rheumatoid arthritis," Arthritis Res. 4:281-289, 2002.

Yu, J. et al., "An essential role for IL-17 in preventing pathogen-initiated bone destruction: recruitment of neutrophils to inflamed bone requires IL-17 receptor—dependent signals," Blood 109: 3794-3802, 2007.

Sato, K., et al. Th17 functions as an osteoclastogenic helper T cell subset that links T cell activation and bone destruction. J Exp Med, 203(12), 2673-2682, 2006.

Blocking Antibody

Isotype Control

METHODS OF TREATMENT OF BONE DEGENERATIVE DISEASES

CROSS-REFERENCE TO RELATED APPLICATIONS

This application claims the benefit of and priority to U.S. Provisional Application No. 61/356,637, filed on Jun. 20, 2010, which is incorporated herein by reference in its entirety.

BACKGROUND

1. Field

The present invention relates to compositions and methods for treating osteoporosis and other bone degenerative diseases in subjects in need thereof, such as post-menopausal women.

2. Introduction

Bone is generally believed to be a tissue in a steady state, in which bone formation by osteoblasts and bone resorption by osteoclasts occur continuously. Osteoporosis is a disease that frequently occurs in menopausal and post-menopausal women, and is characterized by an imbalance of activity of osteoclasts and osteoblasts.

Recent evidence indicates that interleukin-17 (IL-17), which is produced primarily by the Th17 subset of $CD4^+$ T cells but can also be produced by a variety of other cell types, is a key cytokine promoting osteoclast formation. IL-17 is an established inducer of receptor activator of NF-κB ligand (RANKL) expression in target cells such as osteoclasts (Gallen, S. L., Arthritis Res. & Therapy 6: 240-247, 2004; Udagawa, N., et al., Arthritis Res. 4:281-289, 2002).

In one recent study, ovariectomized mice genetically deficient for IL-17 Receptor (IL-17 $RA^{-/-}$ mice) were reported as exhibiting enhanced bone loss (Goswami, J., et al., Eur. J. Immunol. 39: 1-9, 2009). The authors of this report proposed that signaling via the IL-17 receptor simultaneously promotes osteoclastogenesis and inhibits adipogenesis. They concluded that IL-17RA signaling protects against estrogen deficiency-induced bone loss. These conclusions imply that promotion of IL-17RA signaling could be therapeutic for osteoporosis. However, their measurements used Dual energy X-ray absorptiometry (DEXA), which is not a precise measurement of bone volume or density in these mice because DEXA is influenced by fat distribution (Formica, C., et al., J. Bone Miner. Res. 10, 1504-1511, 1995; Hangartner, T. N., et al., Bone Miner. 9, 71-81, 1990; Tothill, P., et al., J. Bone Miner. Res. 12, 1908-1921, 1997; Tothill, P., et al., Br. J. Radiol. 72, 661-669, 1999; Wren, T. A., et al., J. Clin. Endocrinol. Metab. 92, 938-941, 2007).

Halofuginone, 7-Bromo-6-chloro-3-[3-[(2S,3R)-3-hydroxy-2-piperidinyl]-2-oxopropyl]-4-quinazolinone (including salts thereof), is a febrifugine analogoue and an established anti-coccidial agent approved by the USDA for the treatment of parasites in poultry and beef. Halofuginone inhibits IL-17 production and TH17 cell differentiation by activating the amino acid starvation response (Sundrud, M. S., et al., Science 324: 1334-1338, 2009). Halofuginone has use as an inhibitor of angiogenesis (US Patent Application Publication 20100029615 of Munchhof et al.). It has also been cited as an anti-sclerodermal agent (U.S. Pat. No. 7,638,480 to Power et al.) and as an inhibitor of collagen synthesis (Granot et al., Biochimica Biophys. Acta 1156: 107-112, 1993). It is also cited as an anti-cancer agent (U.S. Pat. No. 7,713,994 Tsou et al.) US Patent Application Publication 20090123389 of Whitman et al. discloses use of Halofuginone for treating cellulite.

The anti-sclerosis properties of Halofuginone are thought to arise from its ability to inhibit production of type I collagen by fibroblasts, which is the main constituent of fibrous tissue. Halofuginone inhibits collagen α1(I) mRNA and protein levels in a variety of cells, including mouse skin fibroblasts, avian, growth plate chondrocytes; a transformed rat embryo cell line, vascular smooth muscle cells, bovine aortic endothelial cells, and rat liver stellate cells (Bruck et al., Hepatology, 33(2), 379-386, 2001; Choi et al., Arch. Surg., 130(3), 257-261, 1995; Granot et al., Biochim Biophys Acta, 1156 (2), 107-112, 1993). Collagen type II or III were not inhibited in these studies (Choi et al., Arch. Surg., 130(3), 257-261, 1995; Granot et al., Biochim Biophys Acta, 1156(2), 107-112, 1993). Halofuginone is shown to inhibit fibrosis accumulation in rat urethral stricture formation (Nagler et al., J. Urol., 164(5), 1776-1780, 2000), thioacetamide- and dimethylnitrosamine-induced rat cirrhosis (Bruck et al., Hepatology, 33(2), 379-386, 2001; Pines et al., J. Hepatol., 27(2), 391-398 1997), rat pulmonary fibrosis after bleomycin treatment (Nagler et al., Am. J. Respir. Crit. Care Med., 154(4 Pt 1), 1082-1086, 1996), and tight skin (Tsk)+ and cGvHD-afflicted mice (Levi-Schaffer et al., J. Invest. Dermatol., 106(1), 84-88, 1996; McGaha et al., J. Invest. Dermatol., 118(3), 461-470, 2002; Pines et al., Biochem. Pharmacol., 62(9), 1221-1227, 2001). The drug was effective whether given orally, locally, or intraperitoneally. The mechanism by which Halofuginone decreases collagen type I is unclear, but seems to require new protein synthesis, since cycloheximide or actinomycin D blocks the suppressive effect of Halofuginone on collagen α1(I) mRNA expression (Halevy et al., Biochem. Pharmacol., 52(7), 1057-1063, 1996). Its antifibrotic effects may be due to inhibition of TGFβ1 signaling (McGaha et al., J. Invest. Dermatol., 118(3), 461-470, 2002), but at concentrations that inhibit IL-17 production, no TGFβ inhibition is seen (Sundrud et al., Science, 324(5932), 1334-1338, 2009). Rather, Halofuginone induces the amino acid starvation response, which through unknown mechanisms prevents IL-17 production and Th17 development, a process that cannot be rescued by forced RORγt expression (Sundrud et al., Science, 324(5932), 1334-1338, 2009). In most animal models of fibrosis, regardless of the tissue, Halofuginone had a minimal effect on collagen content in the control, nonfibrotic animals, whereas it exhibited a profound inhibitory effect in the fibrotic organs. In culture, Halofuginone was effective in reducing collagen synthesis by fibroblasts after they had been stimulated with a profibrotic agents, but had a very small effect on collagen synthesis in control cells (McGaha et al., J. Invest. Dermatol., 118(3), 461-470, 2002). Even in animal models of pre-existing fibrosis, Halofuginone treatment can reduce fibrotic levels to normal levels (Nagler et al., Ann. Surg., 227(4), 575-582, 1998).

Given the promise of Halofuginone in treatment of systemic sclerotic conditions, Phase I-III studies have been performed using the drug topically, as well as a Phase I study for oral administration. The oral study was double-blind and involved 26 healthy, male volunteers receiving between 0.07 to 2.5 mg/d with food. Single, oral doses of 0.07 and 0.5 mg Halofuginone were found to be safe and well tolerated, with no clinically significant adverse events. At 1.5 to 2.5 mg, Halofuginone was moderately tolerated, with incidence of nausea and vomiting associated with dose, escalation. A daily dose of 1.5 mg Halofuginone was designated as the maximal tolerated dose. A later study found that dividing the dose into several daily portions allowed greater intake without increasing gastrointestinal adverse events (Pines et al., Biol. Blood Marrow Transplant, 9(7), 417-425, 2003).

Since earlier studies implicate IL-17 in the pathogenesis of osteoporosis, the inventors tested whether Halofuginone administration post-ovariectomy has an effect on IL-17 production and bone mass, and find Halofuginone to be a novel potential therapeutic for treatment of osteoporosis.

There are several structural analogues of Halofuginone that have been identified and/or synthesized, such as febrifugine, isofebrifugine, Df-1 and Df-2 (Takaya, Y. et al., J. Med. Chem 42: 3163-3166, 1999; Kikuchi, H., et al. J. Med. Chem. 45, 2563-2570, 2002). These molecules have use as anti-malarial agents (Takaya, Y. et al., J. Med. Chem 42: 3163-3166, 1999; McLaughlin, N. P., et al., J. Org. Chem. 2010 75: 518-521, 2010; U.S. Pat. No. 4,632,926 to Giarda et al.; U.S. Pat. No. 3,320,124 to Waletsky et al., U.S. Pat. No. 2,694,711 to Baker et al.)

Halofuginone and its analogs comprise a quinazolinone. Quinazolinones such as Halofuginone and its analogues have the general formula

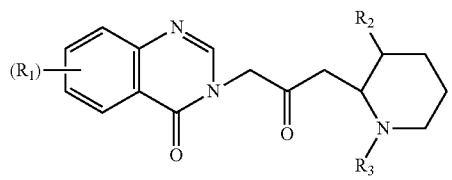

wherein $R_1$ is a hydrogen, a halogen, a nitro, a benzo, a lower alkyl, a phenyl, or a lower alkoxy and can be located at one or more of the 6, 7 or 8 positions on the quinazolinone nucleus; $R_2$ is a hydroxyl, an acetoxy, or a lower alkoxy; and $R_3$ is a hydrogen or a lower alkoxycarbonyl; lower alkyl and lower alkoxy radicals can have from 1 to 6 carbons (U.S. Pat. No. 3,320,124).

Halofuginone and its analogues have also been described as

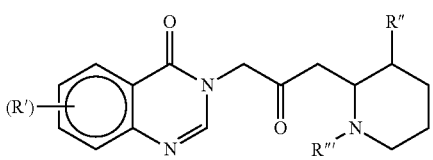

wherein R'=H, halogen, nitro, benzo, alkyl, phenyl or alkoxy; R''=hydroxy, acetoxy or alkoxy; and R'''=H or alkenoxycarbonyl (U.S. Pat. No. 4,632,926). Additional examples of quinazolinone analogues of Halofuginone which are active against coccidiosis include

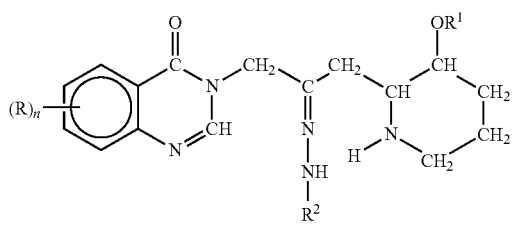

wherein R is an alkyl $C_1$-$C_4$, an alkoxy $C_1$-$C_4$, an alkylthio or a halogen; n is zero, one or two; $R^1$ is a hydrogen atom or an alkyl $C_1$-$C_4$; $R^2$ is a hydrogen atom, an alkyl $C_1$-$C_8$, a cycloalkyl $C_3$-$C_6$ or a phenyl optionally substituted by one or more alkyl $C_1$-$C_4$ or halogen atoms (U.S. Pat. No. 4,632,926).

Kikuchi, H., et al., J. Med. Chem. 45, 2563-2570, 2002 have described several analogues of Halofuginone, including analogues of febrifugine, such as the following compounds:

(1)

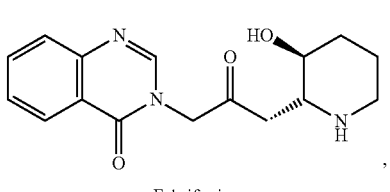

Febrifugine (2)

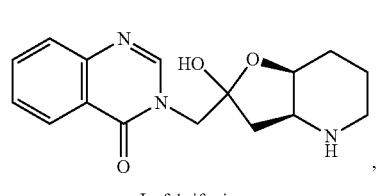

Isofebrifugine (3)

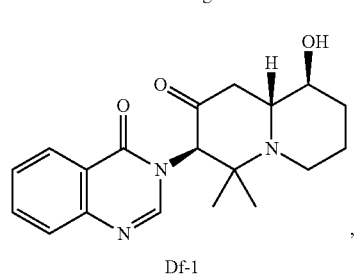

Df-1

(4)

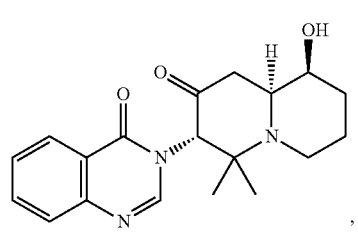

DF-2

(5)

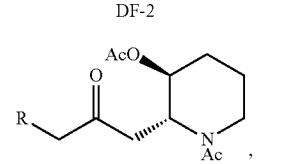

(6)

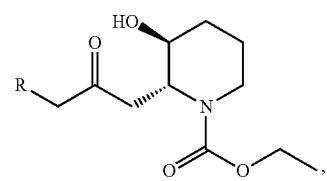

(7)

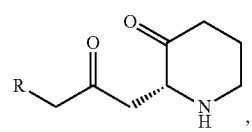

-continued
(8)
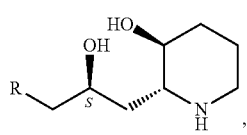
(9)
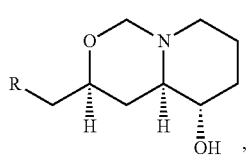
(10)
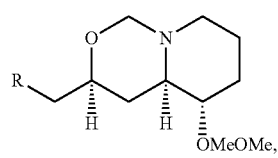
3-{(3S,4aR,5S)-5-Methoxymethyloxy-hexahydropyrido[1,2-c]-[1,3]oxazin-3-ylmethyl}-4(3H)-quinazolinone
(11)
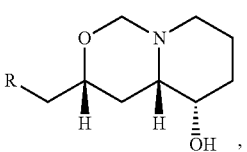
(12)
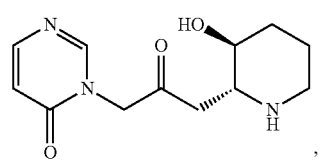
(13)
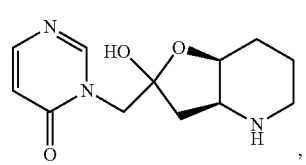
(14)
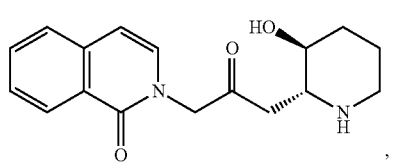
(15)
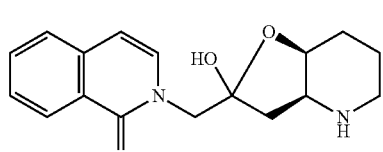
(29)
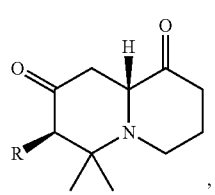
-continued
(30)
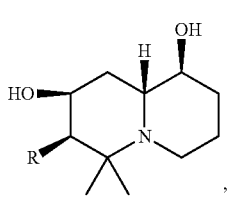
(31)
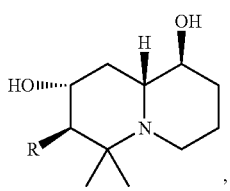
(32)
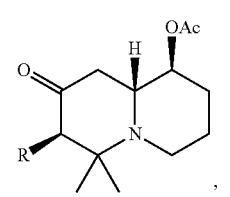
(35)
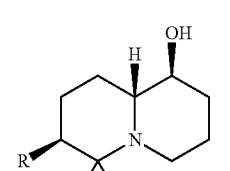
(36)
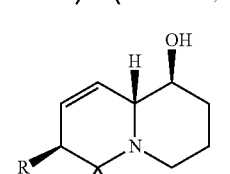
(37)
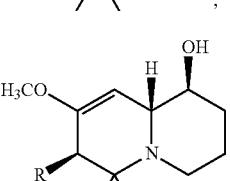
(38)
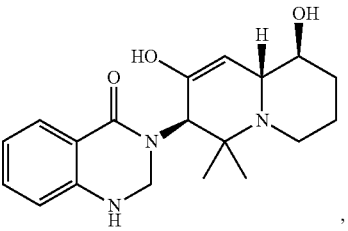
(39)
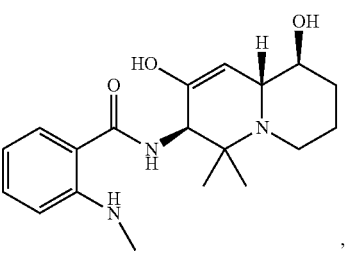

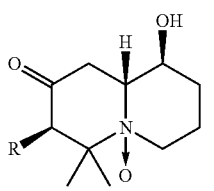

(40)

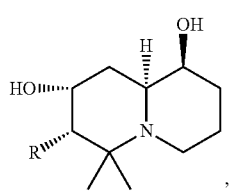

(41)

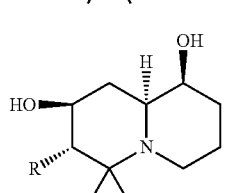

(42)

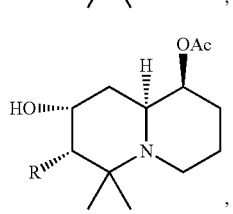

(43)

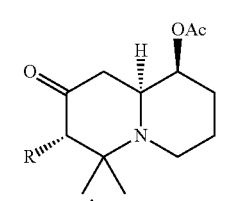

(44)

and

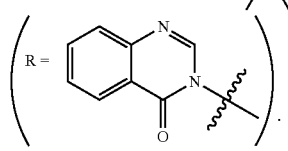

(45)

These workers indicated that the 3"-keto analogue of febrifugine (7) was found to exhibit potential antimalarial activity with high selectivity against *P. falciparum* in vitro. The in vitro activities of the reduction product (8, $EC_{50}=2.0\times10^{-8}$ M) of febrifugine at C-2' and its cyclic analogues 9 and 10 ($EC_{50}=3.7\times10^{-9}$ and $8.6\times10^{-9}$ M, respectively) were found to be strongly active and selective. Additionally, the Dess-Martin oxidation product of 3 was found to be strongly active with high selectivity against *P. falciparum*. The authors concluded that a structure-activity relationship study (SAR) demonstrated that the 4-quinazolinone ring and the presence of a 1"-amino group and C-2', C-3" O-functionalities are crucial in the anti-malarial activity of febrifugine. Anti-malarial activities of febrifugine, isofebrifugine, Df-1, Df-2 and various derivatives thereof are listed in table 1 and table 2.

TABLE 1

Antimalarial Activities of Febrifugine (1) and Isofebrifugine (2) Derivatives in Vitro

| compound | antimalarial activity[a] | cytotoxicity[b] | selectivity[c] |
|---|---|---|---|
| 1 | $7.0 \times 10^{-10}$ | $1.7 \times 10^{-7}$ | 243 |
| 2 | $3.4 \times 10^{-9}$ | $1.8 \times 10^{-7}$ | 53 |
| 5 | $9.1 \times 10^{-7}$ | $>2.9 \times 10^{-5}$ | >32 |
| 6 | $4.8 \times 10^{-6}$ | $>1.7 \times 10^{-5}$ | >3.5 |
| 7 | $2.0 \times 10^{-8}$ | $1.0 \times 10^{-5}$ | 500 |
| 8 | $2.0 \times 10^{-8}$ | $1.5 \times 10^{-5}$ | 750 |
| 9 | $3.7 \times 10^{-9}$ | $3.8 \times 10^{-6}$ | 1027 |
| 10 | $8.6 \times 10^{-9}$ | $2.5 \times 10^{-6}$ | 291 |
| 11 | $8.4 \times 10^{-7}$ | $>2.5 \times 10^{-5}$ | >30 |
| 12 | $6.0 \times 10^{-7}$ | $>1.9 \times 10^{-5}$ | >32 |
| 13 | $4.0 \times 10^{-8}$ | $7.0 \times 10^{-6}$ | 175 |
| 14 | $5.0 \times 10^{-7}$ | $>1.6 \times 10^{-5}$ | >32 |
| 15 | $2.1 \times 10^{-6}$ | $>6.3 \times 10^{-6}$ | >3 |
| chloroquine | $1.8 \times 10^{-8}$ | $3.2 \times 10^{-5}$ | 1778 |
| artemisinin | $1.0 \times 10^{-8}$ | $1.0 \times 10^{-5}$ | 1000 |

[a] Against *P. falciparum* FCR-3.
[b] Against FM3A mouse mammary cells.
[c] Cytotoxicity/antimalarial activity.

TABLE 2

Antimalarial Activities of Df-1 (3) and Df-2 (4) Derivatives in Vitro

| compound | antimalarial activity[a] | cytotoxicity[b] | selectivity[c] |
|---|---|---|---|
| 3 | $1.6 \times 10^{-9}$ | $3.8 \times 10^{-7}$ | 238 |
| 4 | $2.8 \times 10^{-9}$ | $2.4 \times 10^{-6}$ | 857 |
| 29 | $1.9 \times 10^{-9}$ | $5.9 \times 10^{-6}$ | >3105 |
| 30 | $4.0 \times 10^{-7}$ | $2.8 \times 10^{-6}$ | 70 |
| 31 | $3.0 \times 10^{-7}$ | $8.5 \times 10^{-5}$ | 283 |
| 32 | $3.6 \times 10^{-9}$ | $1.3 \times 10^{-6}$ | 361 |
| 35 | $8.3 \times 10^{-7}$ | $>2.2 \times 10^{-5}$ | >27 |
| 36 | $4.8 \times 10^{-6}$ | $>3.2 \times 10^{-5}$ | >7 |
| 37 | $1.3 \times 10^{-6}$ | $>6.6 \times 10^{-5}$ | >51 |
| 38 | $4.2 \times 10^{-7}$ | $>1.6 \times 10^{-5}$ | >38 |
| 39 | $6.0 \times 10^{-7}$ | $>1.7 \times 10^{-5}$ | >28 |
| 40 | $1.0 \times 10^{-7}$ | $>2.9 \times 10^{-5}$ | >290 |
| 41 | $8.0 \times 10^{-7}$ | $>2.4 \times 10^{-5}$ | >30 |
| 42 | $3.4 \times 10^{-6}$ | $>1.0 \times 10^{-4}$ | >28 |
| 43 | $4.0 \times 10^{-7}$ | $>1.1 \times 10^{-5}$ | >28 |
| 44 | $7.0 \times 10^{-6}$ | $>2.1 \times 10^{-5}$ | >3 |
| 45 | $1.9 \times 10^{-8}$ | $7.0 \times 10^{-6}$ | 368 |

[a] Against *P. falciparum* FCR-3.
[b] Against FM3A mouse mammary cells.
[c] Cytotoxicity/antimalarial activity.

U.S. Pat. No. RE39,574 E to Pines et al. describes using quinazoline compounds such as Halofuginone for attenuating neovascularization in the treatment of certain malignancies.

There is an ongoing need for drugs and therapies which can be used to treat degenerative bone diseases such as osteoporosis.

SUMMARY

The present inventors have developed new treatments for osteoporosis and other degenerative bone diseases such as, for example, inflammatory osteolysis. In various embodiments, methods and compositions disclosed herein can ameliorate or inhibit the progression of a degenerative bone disease such as osteoporosis or inflammatory osteolysis. In various embodiments, methods and compositions disclosed herein can be used to prevent the occurrence of a degenerative bone disease such as, for example, osteoporosis or inflammatory osteolysis. In some embodiments, the methods comprise administering to a subject having a degenerative bone disease a therapeutically effective amount of a selective Th17 inhibitor, or an inhibitor of IL-17 production by Th17 or other cells. In various embodiments of the present teachings, a selective inhibitor of IL-17 activity or production can be an inhibitor that can modulate the development and/or expansion of Th17 cells by inhibiting, partially or completely, the development of naive T cells into Th17 cells. In some configurations, a selective inhibitor of IL-17 activity or production can be an inhibitor that can cause naive cells to turn away from the Th17 lineage. In some embodiments, a selective inhibitor of IL-17 activity or production can be an inhibitor that alters the development of naive T cells away from the Th17 lineage. In some embodiments, a selective inhibitor of IL-17 activity or production can be an inhibitor that promotes or otherwise induces the developing T cells toward the regulatory T cells (Treg) lineage. In some aspects, a selective inhibitor of IL-17 production of the present teachings can modulate the development and/or expansion of Th17 cells by specifically inhibiting, reducing or otherwise impeding the ability of TGF-β or other Th17-dependent transcription factors, such as RORγt, RORα, interferon regulatory factor 4 (IRF4), the aryl hydrocarbon receptor (AHR), runt-related transcription factor 1 (RUNX1), or Stat3, to promote the expansion of Th17 cells. In various embodiments, an inhibitor of IL-17 production can impair transcription of either IL-17 directly or of regulators of IL-17. In some embodiments, an inhibitor of IL-17 production can inhibit translation of IL-17 protein, or of one or more proteins that regulate IL-17. In some configurations, an inhibitor of IL-17 production can interfere with one or more intracellular regulators of IL-17. In some configurations, an inhibitor of IL-17 production can impair secretion of IL-17, in Th17 or other cell types. Accordingly, the present teachings include compositions comprising an inhibitor of IL-17 activity or IL-17 production.

Furthermore, in some aspects, the present teachings include compositions comprising an inhibitor of Th17 cells or other IL-17 producing cells. In various embodiments, an inhibitor of the present teachings can be Halofuginone, an analogue thereof, or a salt thereof. In various embodiments, a composition of the present teachings can also comprise a second compound such as a statin, retinoic acid or an inhibitor of IL-6 or IL-21. In some embodiments, a method can comprise administering to a subject a therapeutically effective amount of Halofuginone or an analogue thereof or a salt thereof such as Halofuginone HBr for the treatment of osteoporosis or other degenerative bone disease. In some embodiments, a method can comprise administering to a subject a Halofuginone or an analogue thereof or a salt thereof in an amount effective for prevention of osteoporosis or other degenerative bone disease. In some embodiments, a subject can be a mammal such as a human, a companion animal or a farm animal. In some aspects, a subject can be post-menopausal woman. In various configurations, an analogue of Halofuginone can be a quinazolinone, such as a quinazolinone further comprising a substituent attached at the nitrogen adjacent the carbonyl

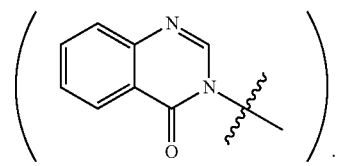

In various configurations, an analogue of Halofuginone can be a compound set forth by Kikuchi, supra, or can have a structure

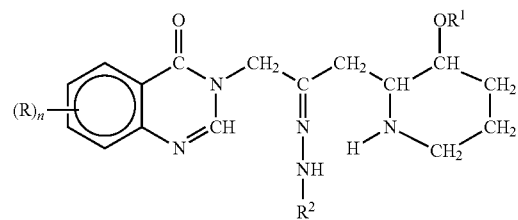

wherein R is an alkyl $C_1$-$C_4$, an alkoxy $C_1$-$C_4$, an alkylthio $C_1$-$C_4$ or a halogen; n is zero, one or two; $R^1$ is a hydrogen atom or an alkyl $C_1$-$C_4$; $R^2$ is a hydrogen atom, an alkyl $C_1$-$C_8$, a cycloalkyl $C_3$-$C_6$ or a phenyl optionally substituted by one or more alkyl $C_1$-$C_4$ or halogen atoms.

In various aspects, a composition of the present teachings can comprise an agent that binds one or more molecular targets for Halofuginone, or otherwise interferes with the binding of Halofuginone and one, or more molecular targets for Halofuginone. In some embodiments, a selective inhibitor of IL-17 activity or production can be a multimer that includes two or more subunits linked together to produce a small molecule inhibitor of the development and/or expansion of Th17 cells or other IL-17 producing cells. In one embodiment, a selective inhibitor of IL-17 activity or production can be a multimer that comprises two or more subunits of Halofuginone (HF) or an analogue of Halofuginone. In various configurations, a multimer can be a homomultimer or a heteromultimer. As used herein, the term "homomultimer" refers to a multimer in which each subunit is the same. As used herein, the term "heteromultimer" refers to a multimer that contains at least two different derivatives of the same subunit or a multimer that contains at least two different types of subunits. In some aspects, in a multimer provided herein, each subunit can be a small molecule inhibitor of the development and/or expansion of Th17 cells or other IL-17 producing cells individually, such that when the subunits are linked together, the multimer exhibits the same or greater ability to inhibit the development and/or expansion of Th17 cells. For example, in some embodiments, a multimer can exhibit a cumulative effect in which the ability of the multimer to inhibit the development and/or expansion of Th17 or other IL-17 producing cells can be greater than the ability exhibited by any one subunit individually. In some aspects, a multimer of the present teachings can exhibit a synergistic effect. Alternatively, in some aspects each subunit of a multimer need not be inhibitory for the development and/or expansion of Th17 or other IL-17 producing cells individually, provided that the multimer is able to inhibit the development and/or expansion of Th17 or other IL-17 producing cells.

In various aspects of the present teachings, in a multimer, the subunits can be linked. Suitable linkers for use in the multimers of the present teachings include, but are not limited to alkyl, alkene, alkyne, ether, ester, or amide linkages; carbon-nitrogen, carbon-sulfur linkages, and any chain using combinations of these linkages. In some embodiments, the linker or linkers can be substituted at one or more positions in the main linker chain to modify linker flexibility, stability or hydrophilicity, including, e.g., substitution linking can be through the $R_1$ positions of each subunit of the multimer, for example, by using an alkynyl linkage. A multimer of the present teachings can contain any number of subunits. For example, a multimer of the present teachings can be a dimer, a trimer, a tetramer, a pentamer, or a hexamer. In various configurations, the number of subunits in the multimer can be between 2 and 30.

In some aspects, a subunit of a multimers disclosed herein can be a compound

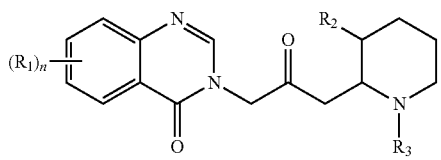

or a salt, isomer, analogue, solvate enantiomer, and/or diasteriomer thereof, wherein $R_1$ can be hydrogen, halogen, nitro, benzo, lower alkyl, phenyl or lower alkoxy; $R_2$ can be hydroxy, acetoxy, or lower alkoxy, $R_3$ can be hydrogen lower alkoxy-carbonyl or lower alkenoxy-carbonyl, and n can be 1, 2, 3 or 4.

A compound or salt thereof of the present teachings can be administered in an amount effective to modulate the production, of IL-17 in a subject. For example, the compound can be febrifugine, or an analogue thereof. In some configurations, a compound can be Halofuginone.

In some embodiments, a dimeric Halofuginone can be synthesized with linkers, and can bind targets of Halofuginone with much higher avidity than Halofuginone alone.

In some embodiments, a compound of the present teachings can be inhibitory to an aspect of the IL-17 pathway for prevention and/or treatment of osteoporosis or other bone degenerative disease. For example, in various aspects, a compound can have activity as an inhibitor of IL-17 Receptor (IL-17R), IL-17 synthesis, or IL-17 activation. Without limitation, in some aspects a compound of the present teachings can be a nucleic acid such as an RNAi (RNA interference)

In various aspects, a compound of the present teachings can be formulated for topical administration, for example, as a film, membrane, foam, gel, or cream. In various aspects, a compound of the present teachings can be formulated for systemic administration. In various aspects, a compound of the present teachings can be formulated as an injectable composition.

The present inventors have shown, in various aspects, that: 1. IL-17 stimulates osteoblastic stromal cells (OBs) to produce RANKL. 2. Osteoblasts express IL-17RA and IL-17RC. 3. IL-17 induces C/EBPβ expression by osteoblasts. 4. OBs express TRAF6. 5. IL-17 can act synergistically with TNFα to promote osteoclastogenesis in the presence of the osteoblast; however, IL-17 can also enhance osteoblast-mediated osteoclast formation without TNFα. 6. IL-17-induced osteoclastogenesis is not mediated by bone marrow macrophage-produced TNFα. 7. IL-17 blocking antibody prevents osteoclast formation when macrophages are grown with osteoblasts in the presence IL-17. 8. IL-17 blocking antibody prevents bone loss associated with estrogen deficiency in mouse model.

DETAILED DESCRIPTION

Figure 1:
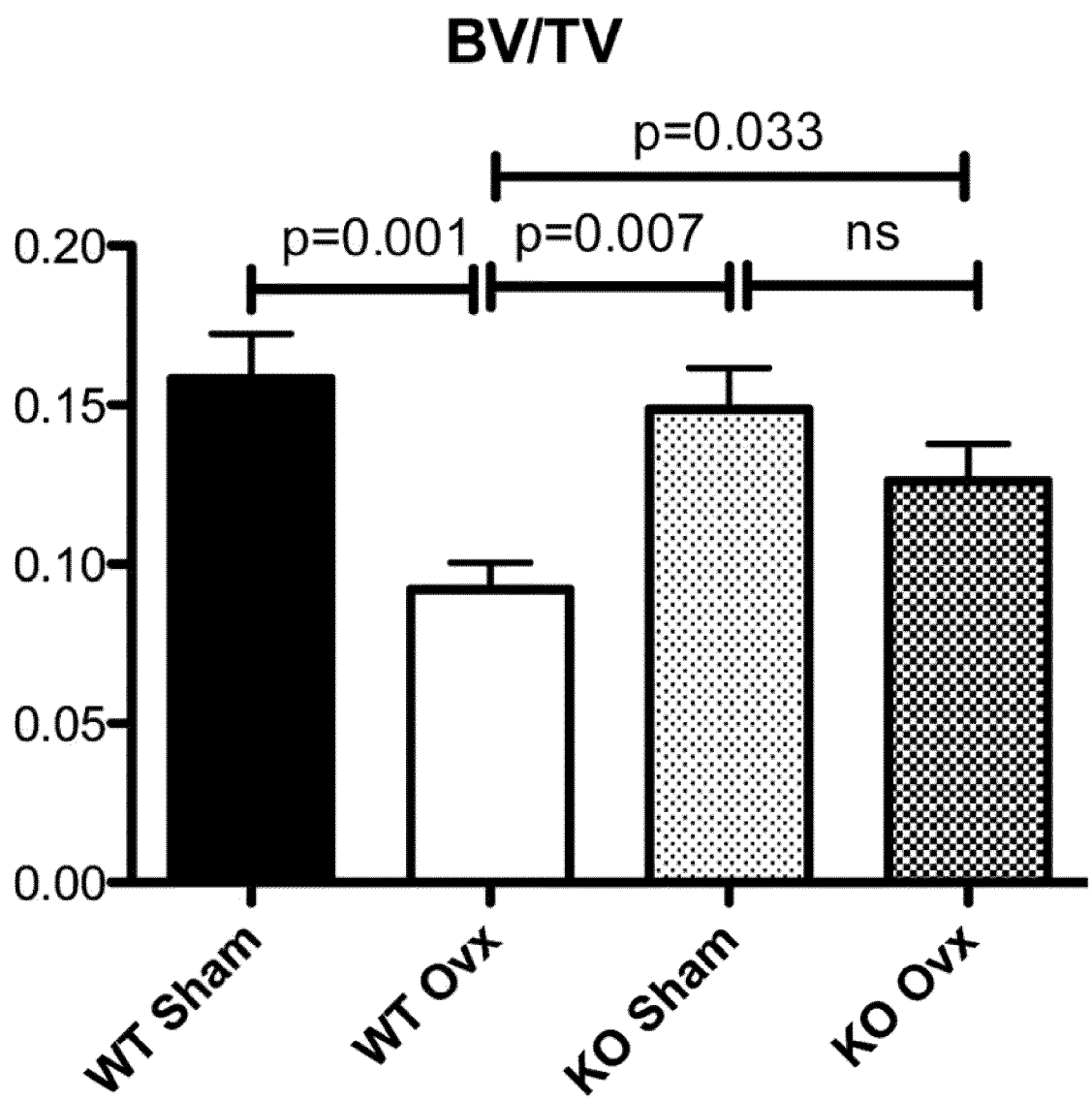
FIG. 1 illustrates IL-17R knockout mice are protected from post-ovariectomy bone loss.

The inventors disclose that treatment with Halofuginone or IL-17 blocking antibody can prevent bone loss.

It is interesting to note that BATF KO mice, which are reported to lack Th17 cells (Schraml et al., Nature, 460(7253), 405-409, 2009), are not protected from ovariectomy-induced bone loss, in contrast to mice treated with Halofuginone or IL-17 blocking antibody.

Methods and compositions described herein utilize laboratory techniques well known to skilled artisans. Such techniques can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999; and Sioud, M., ed. Ribozymes and siRNA Protocols, New York, Springer-Verlag, 2004; Sohail, M., ed., Gene Silencing by RNA Interference: Technology and Application, CRC Press LLC, Boca Raton, Fla., 2005; Schepers, U., RNA Interference in Practice: Principles, Basics, and Methods for Gene Silencing in *C. elegans, Drosophila*, and Mammals, Wiley-VCH Verlag GmbH & Co., Weinheim 2005; and Engelke, D., RNA Interference (RNAi) Nuts & Bolts of RNAi Technology, DNA Press LLC, 2003. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. These publications are incorporated herein by reference, each in its entirety. As used herein, the singular forms "a", "an" and "the" are intended to include the plural forms as well, unless the context indicates otherwise.

In the Examples below, experiments can involve one or more of the following materials and methods.

The present inventors have demonstrated that IL-17 promotes osteoclast formation. The present inventors compared wild type mice with genetic "knock-out" mice lacking the IL-17 receptor that were ovariectomized at 8 weeks of age. Surprisingly, micro CT analysis 4 weeks post ovariectomy showed 30% more bone in the ovariectomized knockout mice compared to wild type. The present inventors developed methods of treating bone degenerative diseases and methods of preventing bone degenerative diseases. In some aspects, these methods comprise inhibiting signaling through the IL-17 pathway. In various embodiments, the methods can comprise administering to a subject an inhibitor of IL-17, an inhibitor of IL-17 Receptor, an inhibitor of RANKL, or an inhibitor of any other component of the IL-17 that contributes to IL-17 signaling, or an agonist of a component of the IL-17 signaling pathway that inhibits IL-17 signaling.

A pharmaceutical composition of the present teachings can be administered by any administration route known to skilled artisans. For example, a pharmaceutical composition of the present teachings can comprise febrifuginone or an analogue such as Halofuginone. In some aspects, febrifuginone or an analogue thereof such as Halofuginone can be administered, for example, by oral administration or by topical (trans-dermal) administration (Pines, M, et al., Biol. Blood Marrow Transplant. 9: 417-415, 2003) or by parenteral administration. In various embodiments, the dosage can be, for example, a dosage effective for inhibiting collagen synthesis. In some embodiments, oral administration can comprise, for example, about 0.07 mg/day, from 0.07 to 2.5 mg/day, or about 2.5 mg/day, and can be given with food during diet controlled meals. In some configurations, administration of Halofuginone can comprise single, oral doses of about 0.07, from 0.07 mg to 0.5 mg, or about 0.5 mg. In some configurations, administration of Halofuginone can comprise daily doses of about 1.5 mg, from 1.5 to 2.5 mg, or about 2.5 mg. In some configurations, a daily dose can be up to 1.5 mg Halofuginone. In some embodiments, Halofuginone can be applied topically, such as through topical application of 0.1% Halofuginone.

Mice: All animals were housed in the animal care unit of the Washington University School of Medicine and were maintained according to guidelines of the Association for Assessment and Accreditation of Laboratory Animal Care. All animal experimentation was approved by the Animal Studies Committee of the Washington University School of Medicine.

Reagents: Halofuginone was purchased from Mingdou Chemical Company Ltd. (Shanghai, China).

Histological analysis: Tibias were harvested, cleaned of soft tissue, and fixed in 10% buffered formalin overnight. For non-decalcified sections, tibias were dehydrated by incubation in an ethanol gradient (20%, 30%, 50%, 70% ETOH, for 30 minutes each). Bones stored in 70% ETOH were then embedded in methylmethacrylate and cut into 5 µm longitudinal sections. Non-decalcified sections were left unstained. For decalcified sections, following fixation, tibias were rinsed in water then incubated in 14% EDTA (pH 7.2) for 7 days with solution changes every 3.5 days. Following decalcification, tibias were rinsed in water then incubated in the ETOH gradient described above. Bones stored in 70% ETOH were then embedded in paraffin, cut into 4 µm longitudinal sections, and stained with TRAP or hematoxylin and eosin for visualization of osteoclasts or osteoblasts, and measurements were made using BioQuant software (Bioquant; Nashville, Tenn.).

Bone formation assay (calcein double labeling): Mice were injected with 7.5 mg/kg calcein (Sigma-Aldrich; St. Louis, Mo.). Five days later mice were injected again, and tibias were harvested after an additional 2 days for histologic analysis. Dynamic assessment of trabecular bone formation was determined on non-decalcified sections using BioQuant software (Bioquant; Nashville, Tenn.). This software provided measures of bone surface, percent single-(sLS/BS) and double-labeled (dLS/BS) bone surface, mineralizing surface (MS/BS), mineral apposition rate (MAR), and bone formation rate (BFR/BS). Trabecular bone measurements were taken from a region encompassing a 500 µm-long field, across the width of the bone (located 100 µm below the growth plate). For each animal, 2 serial sections were analyzed and the measurements averaged. Pictures were obtained using an Olympus 1×51 fluorescent microscope fitted with Olympus DP70 camera (Olympus; Center Valley, Pa.).

Cell culture: Osteoclasts were grown in alpha10 media, containing alpha-MEM (Sigma Aldrich, St. Louis, Mo.), 10% fetal calf serum (Hyclone, Waltham, Mass.), 100 U/mL penicillin and 100 ug/mL streptomycin. Plat-E retrovirus packaging cells were purchased from Cell Biolabs, Inc. (San Diego, Calif.) and maintained in DMEM media (Cellgro, Manassas, Va.) containing 10% fetal calf serum (Hyclone, Waltham, Mass.), and 2 mM L-glutamine (Gibco, Carlsbad, Calif.). Osteoclasts were differentiated from bone marrow as described (Zhao et al., Dev. Cell, 14(6), 914-925, 2008). Briefly, bone marrow was extracted from mice and cultured in the presence of 10% CMG 14-12 supernatant (Takeshita et al., J. Bone Miner. Res., 15(8), 1477-1488, 2000), a M-CSF-containing cell supernatant. After 4 days, cells were lifted and replated on plastic or bovine bone fragments in alpha10 media supplemented with 2% CMG and 100 ng/mL recombinant RANKL. Bone-grown cells were fixed in 4% paraformaldehyde 6 or 7 days after plating. Plastic-grown cells were fixed on days 3, 4, and 5 in 4% paraformaldehyde/PBS for osteoclastogenesis analysis or lysed on various days for immunoblot analysis.

RT-PCR: RNA was isolated using RNeasy kits (Qiagen); RLT lysis buffer was supplemented with β-mercaptoethanol (1%). Purified RNA was treated with DNase I (Invitrogen; Carlsbad, Calif.) prior to reverse transcription (RT). RT was performed using SuperScript III (Invitrogen). A negative control using RNA not subjected to reverse transcription was included in each assay. Quantitative PCR (qPCR) was performed using Applied Biosystems's (Foster City, Calif.)

Power SYBR green master mix and gene specific primers. The qPCR reaction was run on Applied Biosystem's ABI Prism 7000. Transcript levels were normalized to cyclophilin.

Flow Cytometry: Spleen cells were prepared by gently crushing the tissue and filtering through a 40-μm cell strainer (BD Falcon). Cells were harvested, centrifuged, and incubated in red blood cell (RBC) lysis buffer. In stimulation experiments, cells were incubated in 50 ng/ml PMA and 500 ng/ml ionomycin (Sigma-Aldrich) for 4 h at 37° C. Brefeldin A (Sigma-Aldrich) was added during the last 2 h of culture at 10 μg/ml. Cells were stained with LIVE/DEAD Fixable Dead Cell Stain Kits (Molecular Probes, Invitrogen) followed by the appropriate surface antibody (anti-CD4) for 20 min at 4° C. Stained cells were fixed in 2% paraformaldehyde for 20 min at RT before permeabilization with 0.05% saponin. Intracellular staining for the cells was conducted at 4° C. for 30 min using Alexa Fluor 488 anti-mouse IL-17A (1:1000 dilution) (eBioscience). To determine background levels of cytokine staining, a set of cells was not stimulated, but was treated with brefeldin A and stained for intracellular cytokines, as was done for experimental cells. Samples were gated on live cells using the above LIVE/DEAD cell stain. All samples were analyzed on a FACSCalibur or FACSCanto (BD) and data were analyzed with FlowJo software (TreeStar). A total of 30,000 events were collected per sample.

Osteoclastogenesis: Osteoclasts were grown on plastic in 48-well plates for 3-5 days and fixed with 4% PFA, as described above. TRAP staining on fixed cells was performed using a commercially available kit according to the manufacturer's instructions (Sigma, St. Louis, Mo.). All TRAP+ cells with at least three nuclei were counted, with 2-3 wells counted per genotype.

Calvaria osteoblast isolation and culture: Whole calvaria were extracted from 3-4 day old pups and cleaned of soft and periostial tissue. Osteoblasts were liberated by 3×20 minute collagenase treatment at 37 degrees, shaking. Osteoblasts were transduced with appropriate virally expressed proteins when 50% confluent, selected with the appropriate antibiotic for 4 days, then plated for experiments. For cocultures, BMMs were cultured for 4 days prior to being lifted and then cultured with osteoblasts in α-MEM media containing pen/strep, 10% FBS and 10 nM VitD3, plus IL-17 or other cytokines where indicated.

Microcomputed tomography and ovariectomy: Trabecular volume in the distal femoral metaphysis (right leg) was measured using in vivo microcomputed tomography (vivaCT 40, Scanco Medical, Brüttisellen, Switzerland) while the mice were anesthetized with isofluorane. A threshold linear attenuation coefficient of 1.2 cm-1 was used to differentiate bone from non-bone. A threshold of 220 was used for evaluation of all scans. 30 slices were analyzed, starting with the first slice in which condyles and primary spongiosa were no longer visible. Measurements were made 28 days after sham operation or ovariectomy (ovx), unless otherwise indicated. Measurements included bone volume/total volume (BV/TV), connectivity density (Conn. Dens), structure model index (SMI), trabecular separation (Tb.Sp), trabecular thickness (Tb.Th), and trabecular number (Tb.N). For ovariectomies, all mice were aged 8 weeks at time of ovx. Mice were anesthetized with ketamine/xylene delivered by intraperitoneal injection, and ovaries were removed through two small dorsal incisions. Sham operated mice were anesthetized and opened equivalently, but ovaries were not removed.

MRI: Measurements of body composition were performed using the magnetic resonance imaging facility located at the Animal Model Research Core at Washington University (CNRU grant NIB P30 DK56341).

Serum Ctx measurements: Blood was collected by cheek puncture after 6 hours starvation. Plasma was obtained using plasma separator tubes with lithium heparin (Becton Dickinson). Serum CTx-I, a specific marker of osteoclastic bone resorption, was measured using a RatLaps ELISA kit from Nordic Bioscience Diagnostics A/S.

Statistics: All data were analyzed with Prism software (Graphpad, San Diego, Calif.), using two-tailed unpaired Student's t tests, unless otherwise indicated. Error bars represent standard deviation.

EXAMPLES

The following examples are illustrative and are not intended to be limiting of any claim.

Example 1

This example illustrates IL-17R deficiency or treatment with an IL-17 blocking antibody protects mice from bone loss induced by estrogen deficiency.

Figure 2:
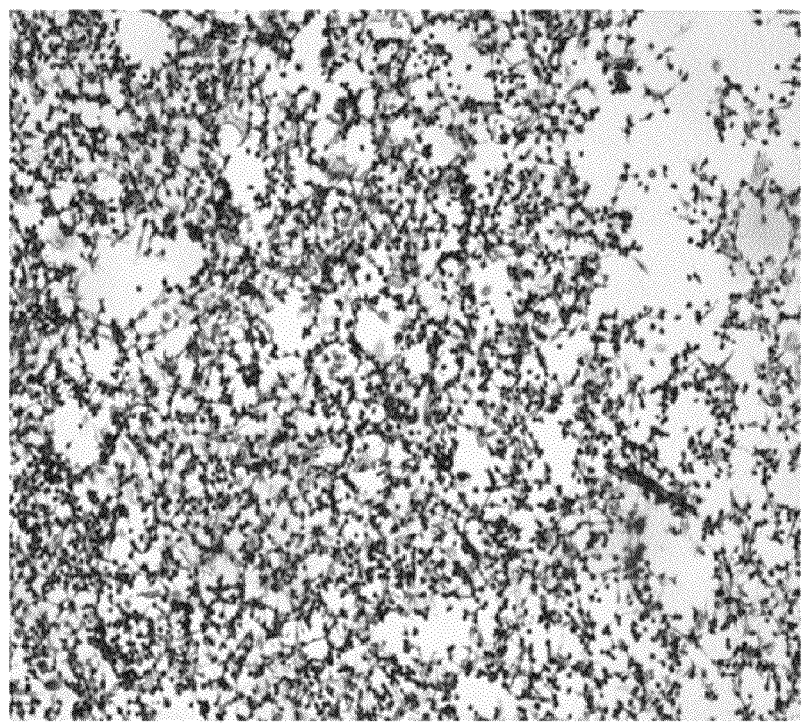
FIG. 2 illustrates IL-17 blocking antibody prevents osteoclast formation in coculture with IL-17.
Figure 2:
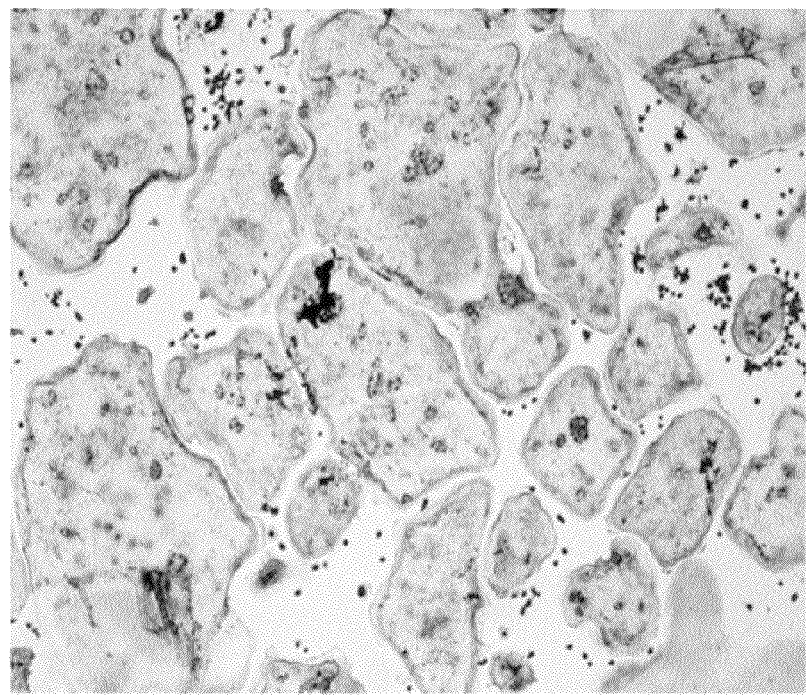
Figure 3:
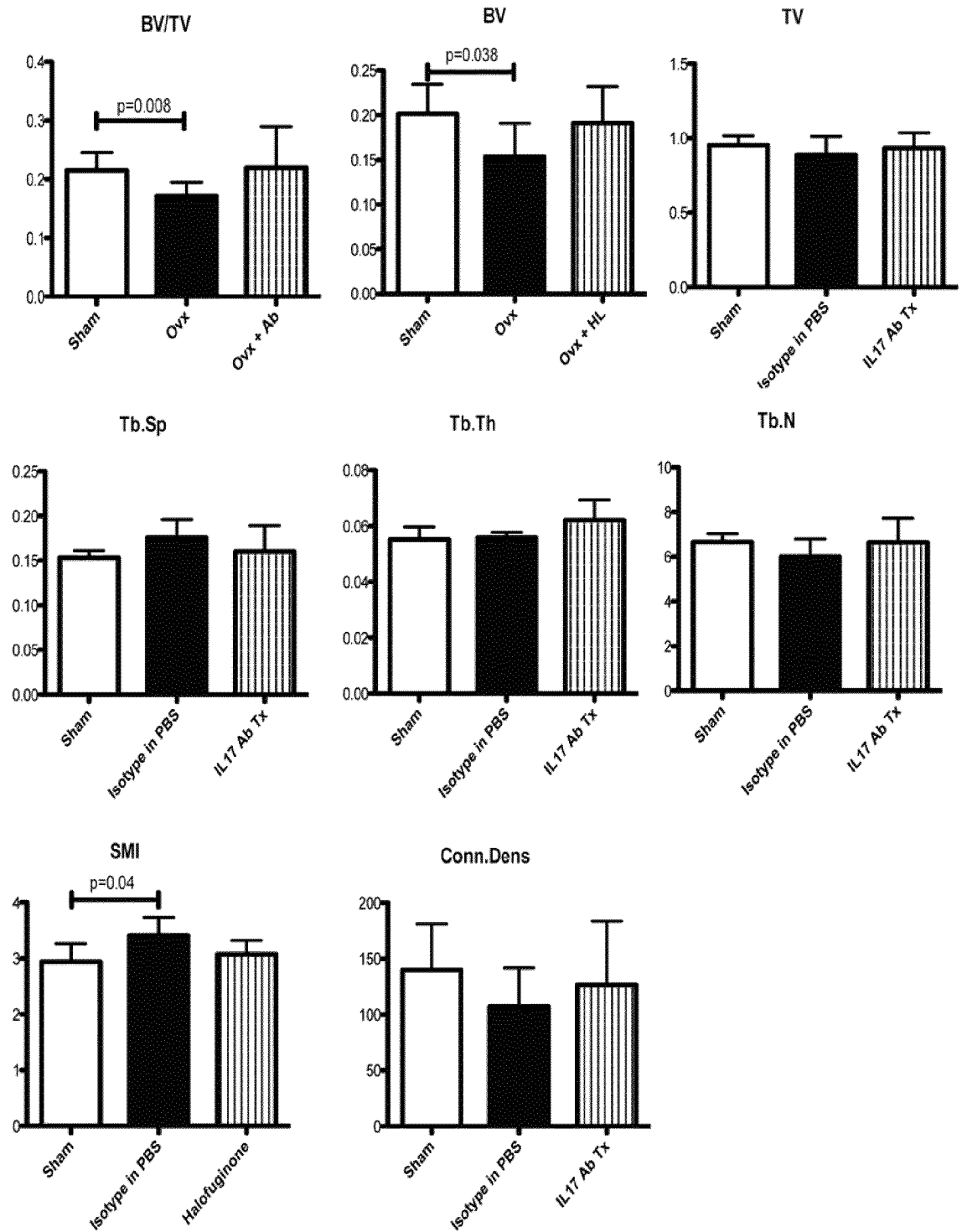
FIG. 3 illustrates IL-17 blocking antibody begins to protect mice from ovariectomy-induced bone loss at two weeks.
Figure 4:
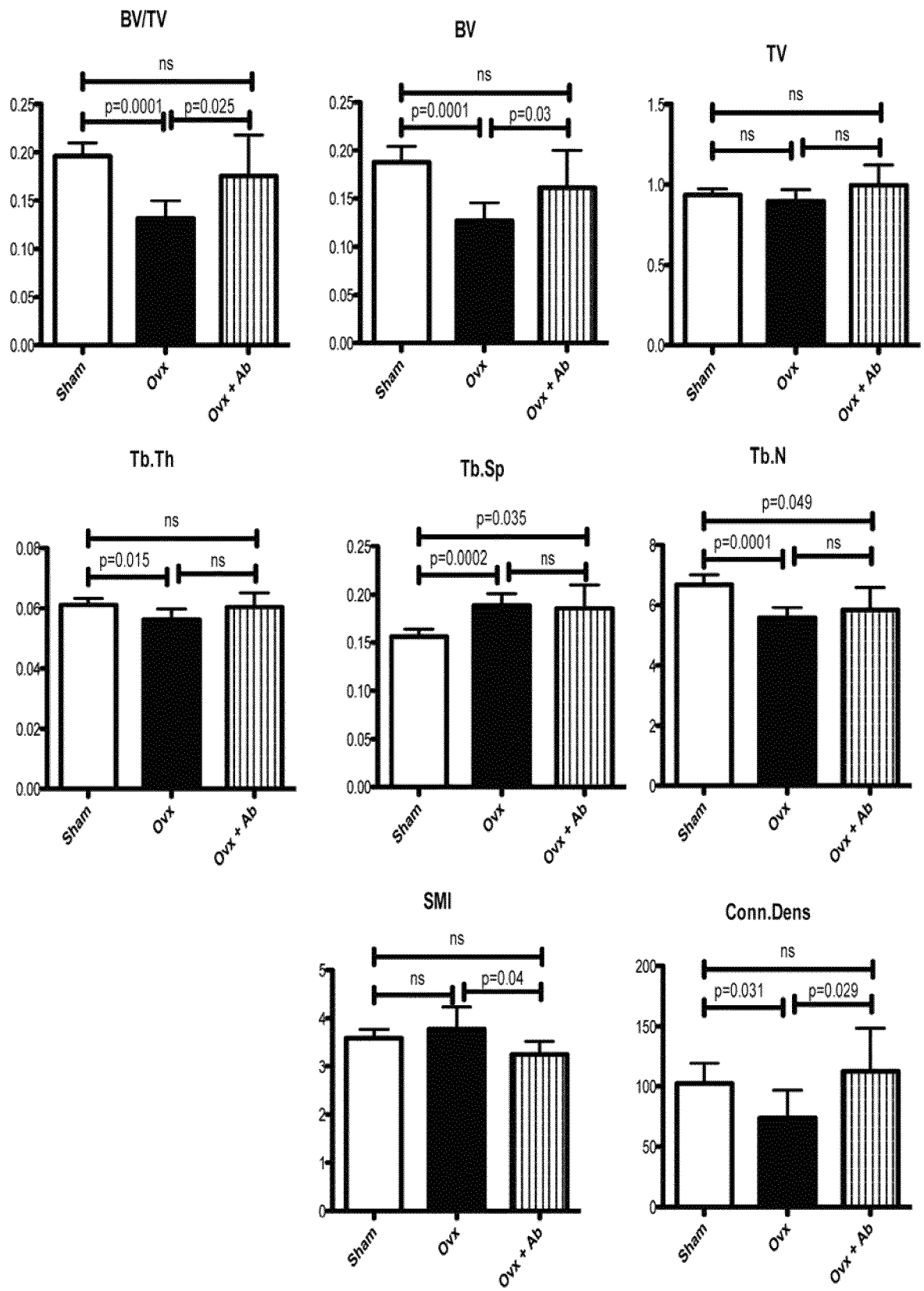
FIG. 4 illustrates an IL-17 blocking antibody protects from ovariectomy-induced bone loss at four weeks.

To test whether IL-17 signaling is important in the pathogenesis of osteoporosis, the inventors mimicked the most common human form of osteoporosis, that of estrogen deficiency, by removing ovaries (ovx) in mice. Wild-type and IL-17 knockout mice were subjected to ovx or sham procedure. Four weeks later, Micro-CT, a sensitive and specific measure of bone volume, was used to assess trabecular Bone Volume per Total Volume measured in the distal femora. While WT mice exhibited significant bone loss after ovx, minor, non-significant changes were observed in IL-17R KO animals (FIG. 1). To further establish the role of IL-17 in this process, the inventors selected an IL-17 blocking antibody for its ability to inhibit osteoclastogenesis in a coculture of bone marrow macrophages (BMMs) with osteoblasts and IL-17. BMMs were cultured with osteoblasts in the presence of Vitamin D (10 nM), IL-17 blocking antibody or isotype control. Osteoblast cells were lifted after 8 days, and osteoclasts were Trap stained (FIG. 2). Both two weeks (FIG. 3) and four weeks (FIG. 4) post-ovx, injection of the blocking antibody protected animals from bone loss, while injection of an isotype control antibody had no effect. Ovariectomized mice (n=5-7 mice per group) were treated with IL-17 blocking antibody or isotype control for two and four weeks and distal femora were analyzed by micro-CT. These data suggest IL-17 is important in the pathogenesis of osteoporosis, and suggest pharmacologic inhibition with either antibody against IL-17 may ameliorate osteoporosis induced by estrogen loss.

Example 2

This example illustrates IL-17 stimulates osteoclastogenesis indirectly through the osteoblast.

Figure 5:
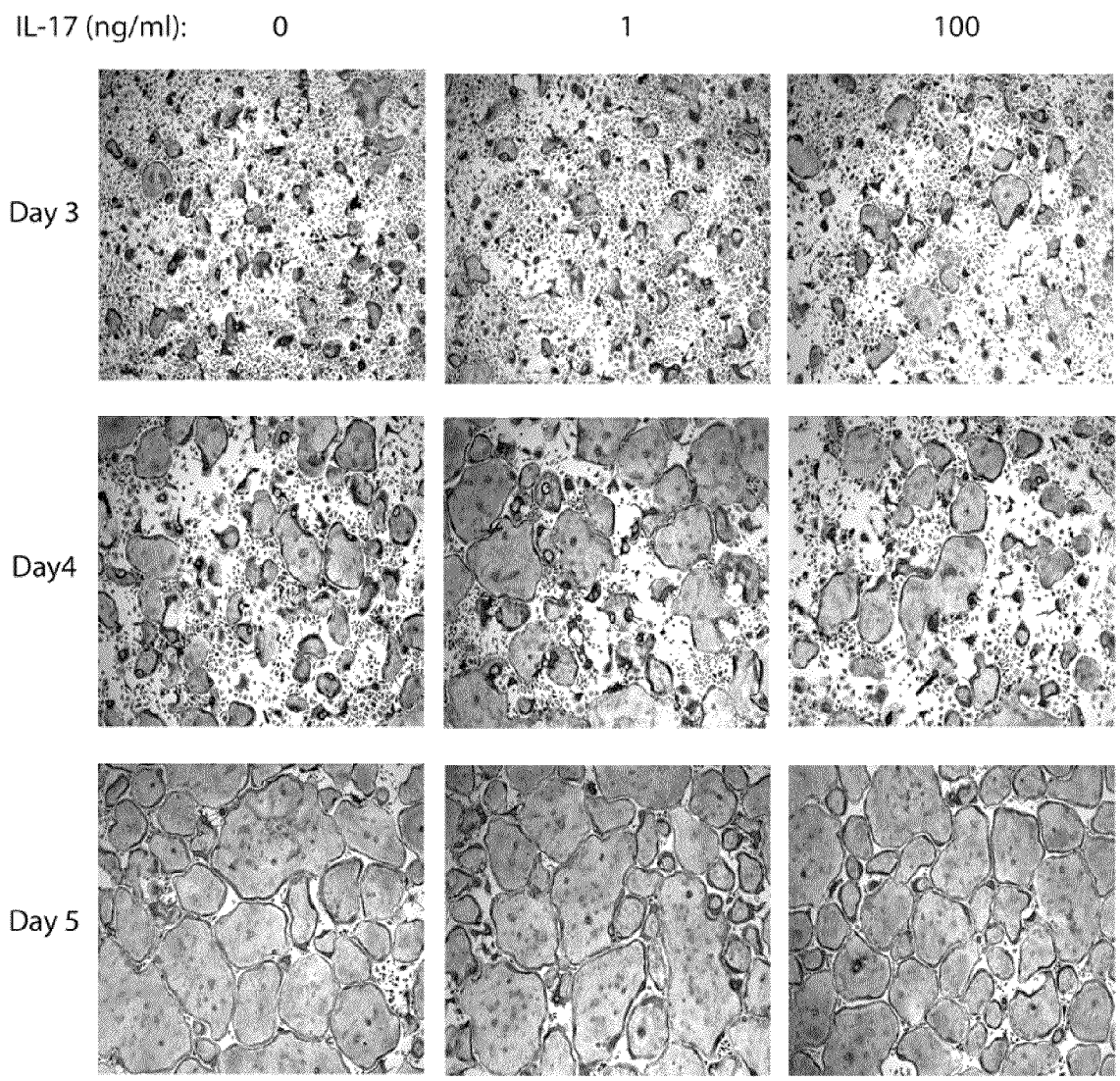
FIG. 5 illustrates IL-17 does not directly affect osteoclast formation.
Figure 6:
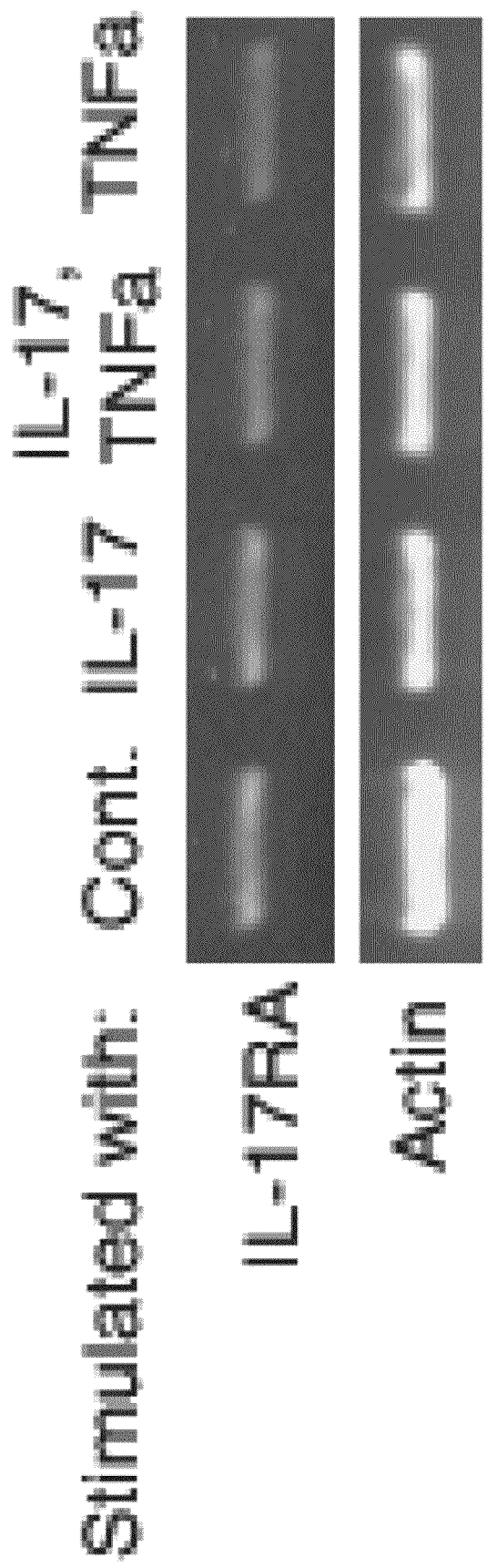
FIG. 6 illustrates the IL-17 receptor is expressed in primary osteoblasts.
Figure 7:
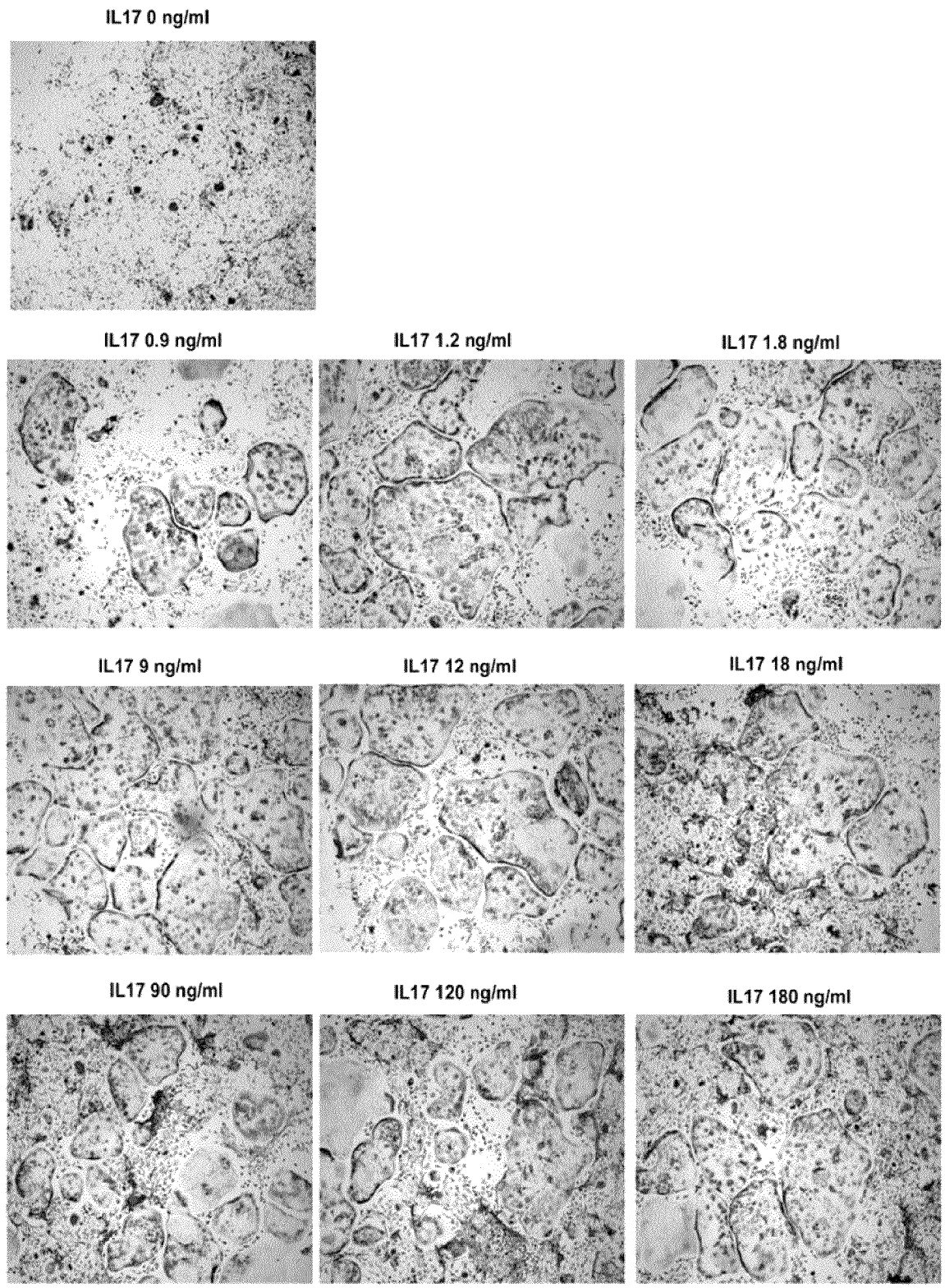
FIG. 7 illustrates IL-17 potentially enduces osteoclastogenesis in coculture.
Figure 8:
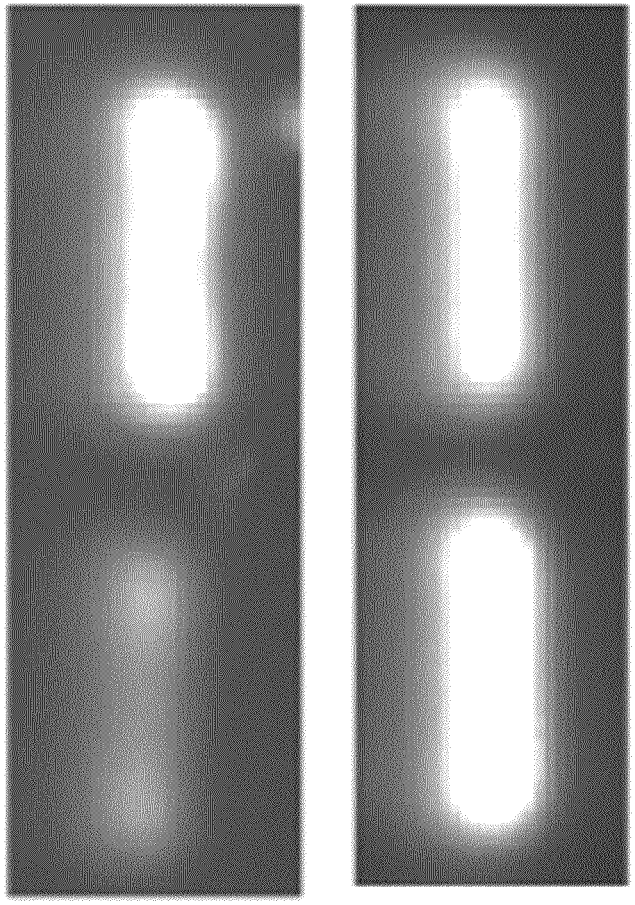
FIG. 8 illustrates RANKL expression is induced by IL-17.
Figure 9:
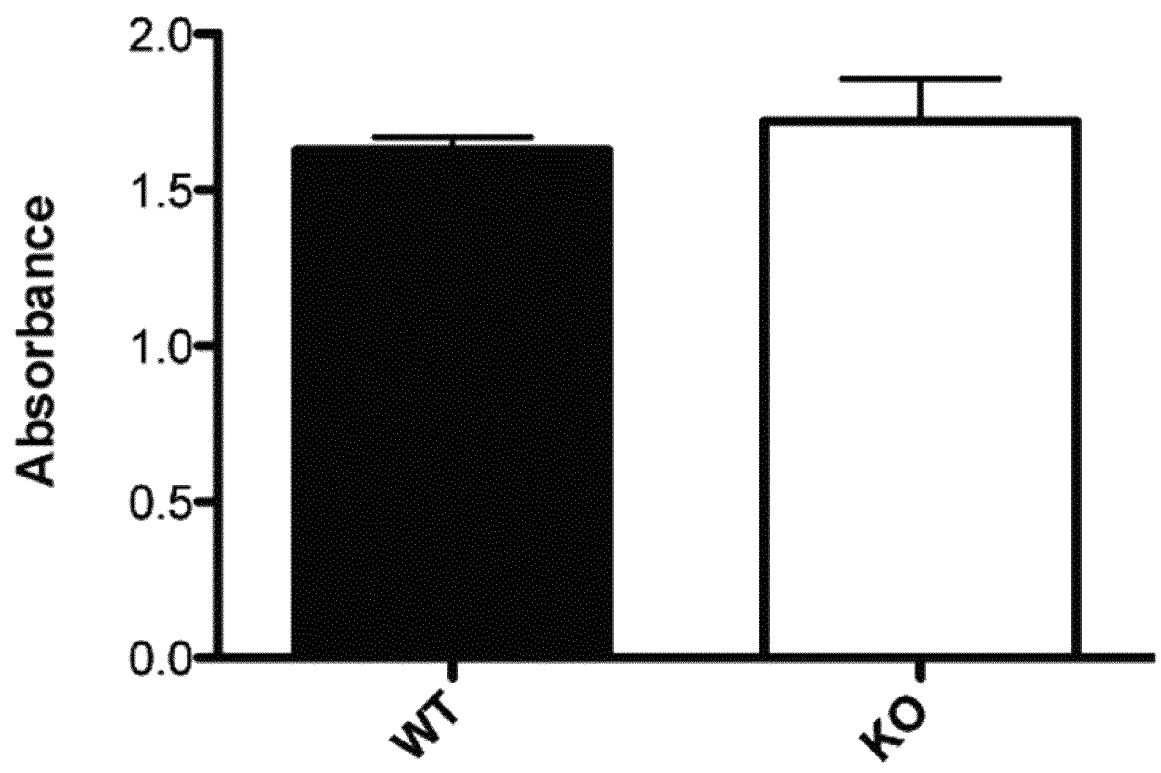
FIG. 9 illustrates IL-17 does not affect osteoblast proliferation.

Since different groups report IL-17 having both a direct and indirect effect on osteoclast development, the inventors first cultured BMMs in the presence of M-CSF (20 ng/ml), RANKL (100 ng/ml), and varying concentrations of IL-17 for 3, 4, 5 days, then fixed, Trap stained, and observed no differences in osteoclast formation (FIG. 5). To test the function of IL-17 signaling in the osteoblast, the inventors first determined the IL-17 receptor is expressed in osteoblasts, and its expression is unaffected by TNFα or IL-17 stimulation. Primary osteoblasts were stimulated with vehicle control, IL-17 (10 ng/ml), TNF (5 ng/ml), or a combination of the two for 24 hours, and RT-PCR for the IL-17 receptor and actin was performed (FIG. 6). Next the inventors cultured BMMs in combination with primary osteoblasts, Vitamin D, and varying IL-17 concentrations. Osteoblasts were lifted, then osteoclasts were fixed and TRAP stained. IL-17 potently induced osteoclast formation, even at low levels (FIG. 7). Primary osteoblasts were stimulated with IL-17 or vehicle control for 24 hours, and RT-PCR was performed using primers for RANKL or actin. RANKL mRNA expression in the osteoblast is induced by IL-17 (FIG. 8), explaining the cytokine's pro-osteoclastogenic effect. IL-17 receptor WT and KO osteoblasts were cultured with IL-17 (10 ng/ml) and BrdU for 24 hours, after which BrdU incorporation was measured by absorptiometry. IL-17 does not affect osteoblast proliferation (FIG. 9). This suggests IL-17 is unable to directly induce osteoclastogenesis, but instead acts through the osteoblast.

Example 3

This example illustrates Halofuginone protection from osteoporosis.

Figure 10:
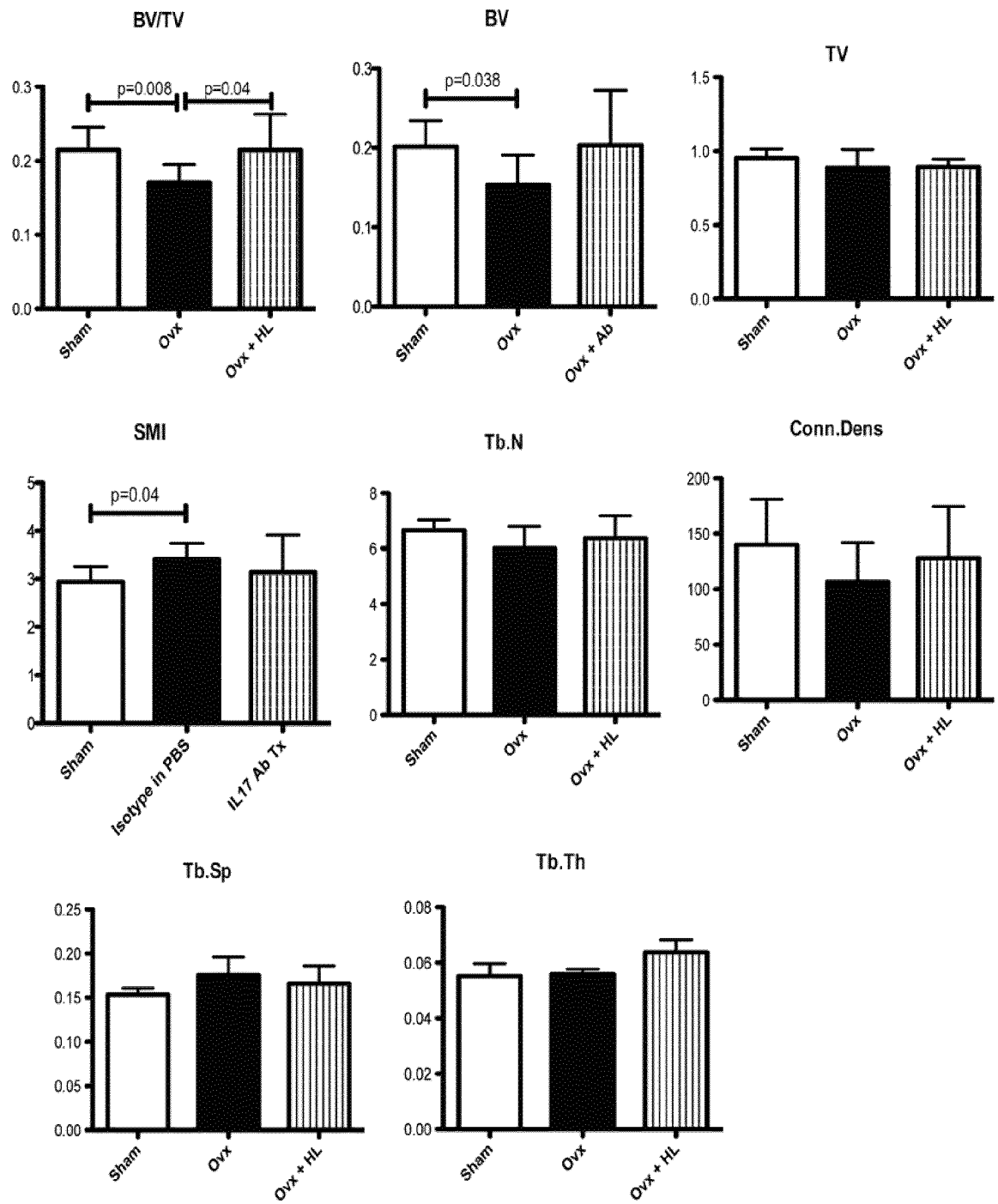
FIG. 10 illustrates Halofuginone protects from ovariectomy-induced bone loss at two weeks.
Figure 11:
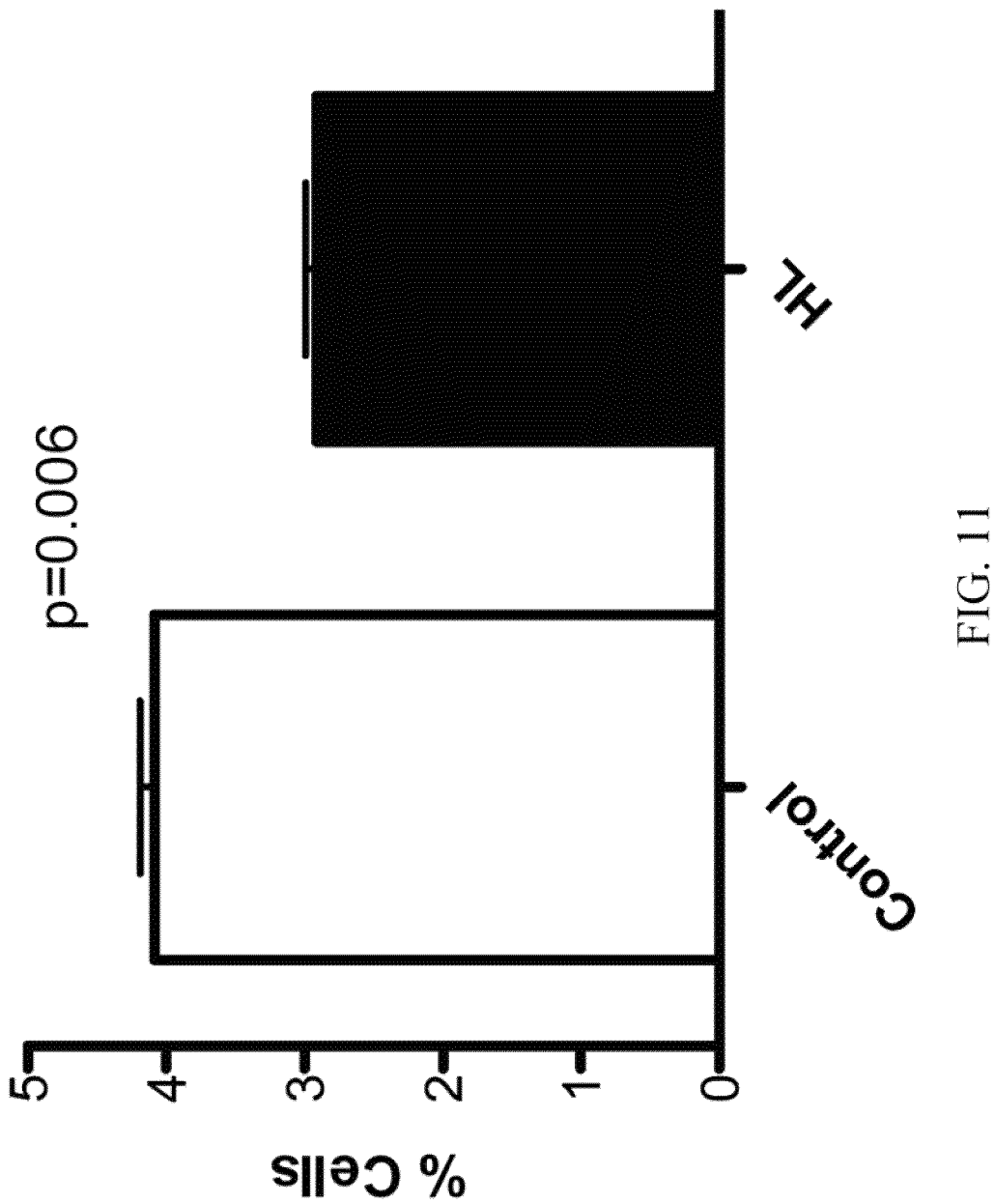
FIG. 11 illustrates Halofuginone treatment reduces Th17 cells after two weeks.
Figure 12:
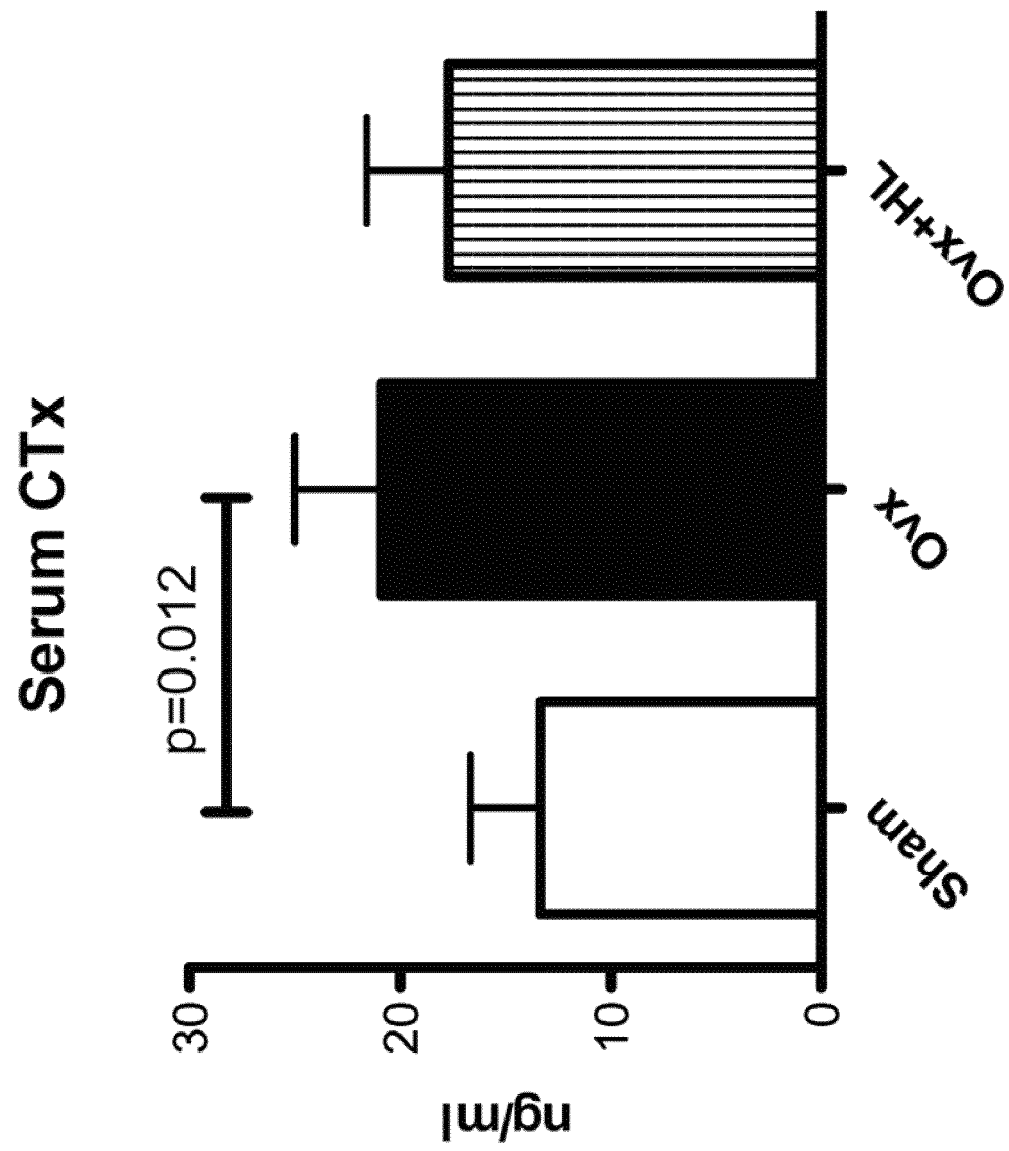
FIG. 12 illustrates Halofuginone treatment reduces serum CTx.
Figure 13:
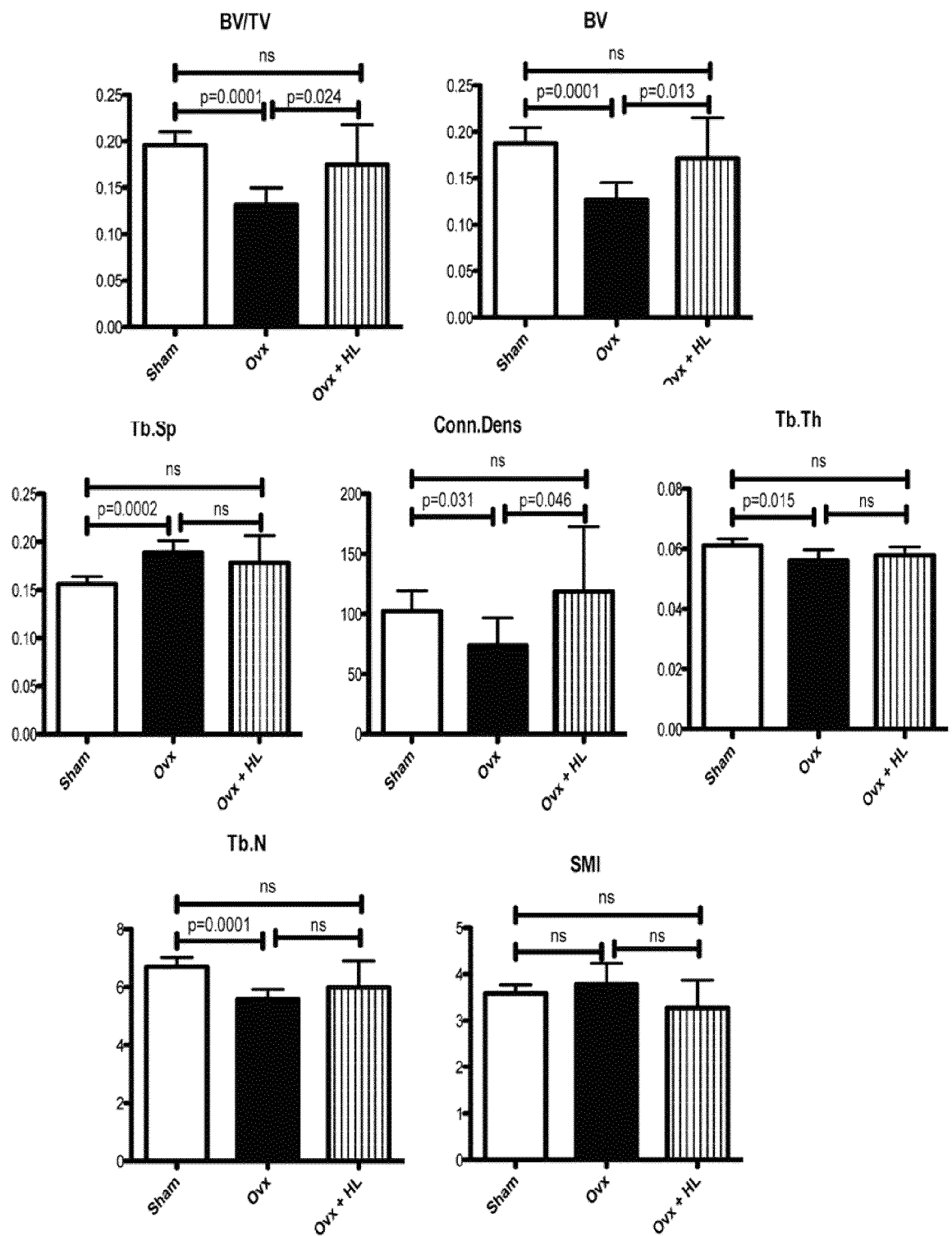
FIG. 13 illustrates Halofuginone protects from ovariectomy-induced bone loss at four weeks.

To mirror the most common form of osteoporosis in humans, an estrogen-deprived state was produced by ovariectomizing mice. Beginning the day of ovx, mice were treated with vehicle or Halofuginone at a dose reported to inhibit IL-17 production (Sundrud et al., Science, 324(5932), 1334-1338, 2009). After two weeks, distal femora were analyzed by micro-CT. Bone volume (BV) was significantly reduced in vehicle treated ovx mice relative to sham, but not in ovx mice treated with Halofuginone (FIG. 10). Bone volume per total volume (BV/TV) was significantly lower in vehicle treated ovx mice compared with either sham or Halofuginone treated ovx mice. The Structure Model Index (SMI), trabecular number (Tb.N), connective density (Conn.Dens), trabeculat space (Tb.Sp), and trabecular thickness (Tb.Th) were also determined. Mice were treated with Halofuginone (HL) or vehicle control daily for two weeks, beginning the day of ovx. Splenic cells were harvested, stimulated with ionomycin, and analyzed by flow cytometry, gating on live cells. Flow cytometry analysis of spleen cells showed the percentage of CD4+ T-cells producing IL-17 was significantly reduced in Halofuginone treated mice after two weeks (FIG. 11). Carboxy-terminal collagen crosslinks (CTx) are released from the bone upon resorption, and serum levels are used to measure levels of systemic bone resorption (Rosen et al., Calcif. Tissue Int., 66(2), 100-103, 2000). Ovariectomized mice (n=5 mice per group) were treated with vehicle or HL daily and after two weeks serum was collected and analyzed by ELISA for CTx. Vehicle treated mice have significantly higher levels of serum CTx, while Halofuginone treated mice have a blunted, non-statistically significant, increase in the serum marker of bone resorption relative to sham operated mice (FIG. 12). Ovariectomized mice (n=5-7 mice per group) were treated with vehicle or HL daily for four weeks and distal femora were analyzed by micro-CT. By four weeks, BV/TV, BV, connectivity density, trabecular thickness, and trabecular number were all significantly reduced in ovx mice compared with sham, but not in Halofuginone treated ovx mice relative to sham (FIG. 13). These data indicate Halofuginone treatment after ovx protects mice from bone loss associated with the estrogen-deprived state.

Example 4

This example illustrates Halofuginone does not directly, affect osteoclast formation or bone formation.

Figure 14:
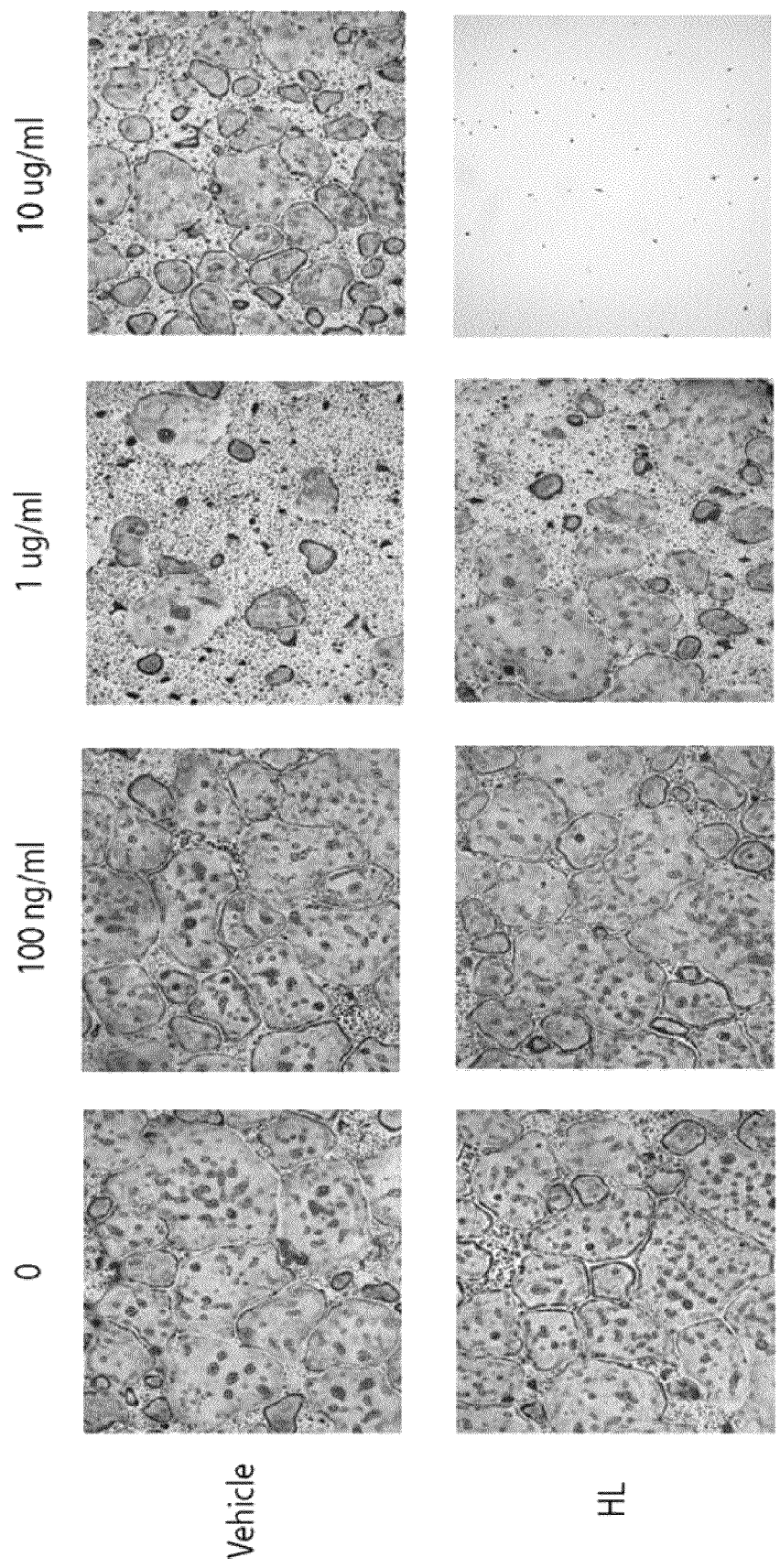
FIG. 14 illustrates Halofuginone does not directly affect osteoclastogenesis.

To exclude the possibility that Halofuginone directly inhibits osteoclasts, bone marrow macrophages were cultured in RANKL (100 ng/ml) and M-CSF plus varying concentrations of Halofuginone or equivalent volume of vehicle for five days, then fixed and TRAP stained. While 1.0 ug/ml was toxic to macrophages in the culture, other concentrations had no effect on osteoclast formation (FIG. 14).

Figure 15:
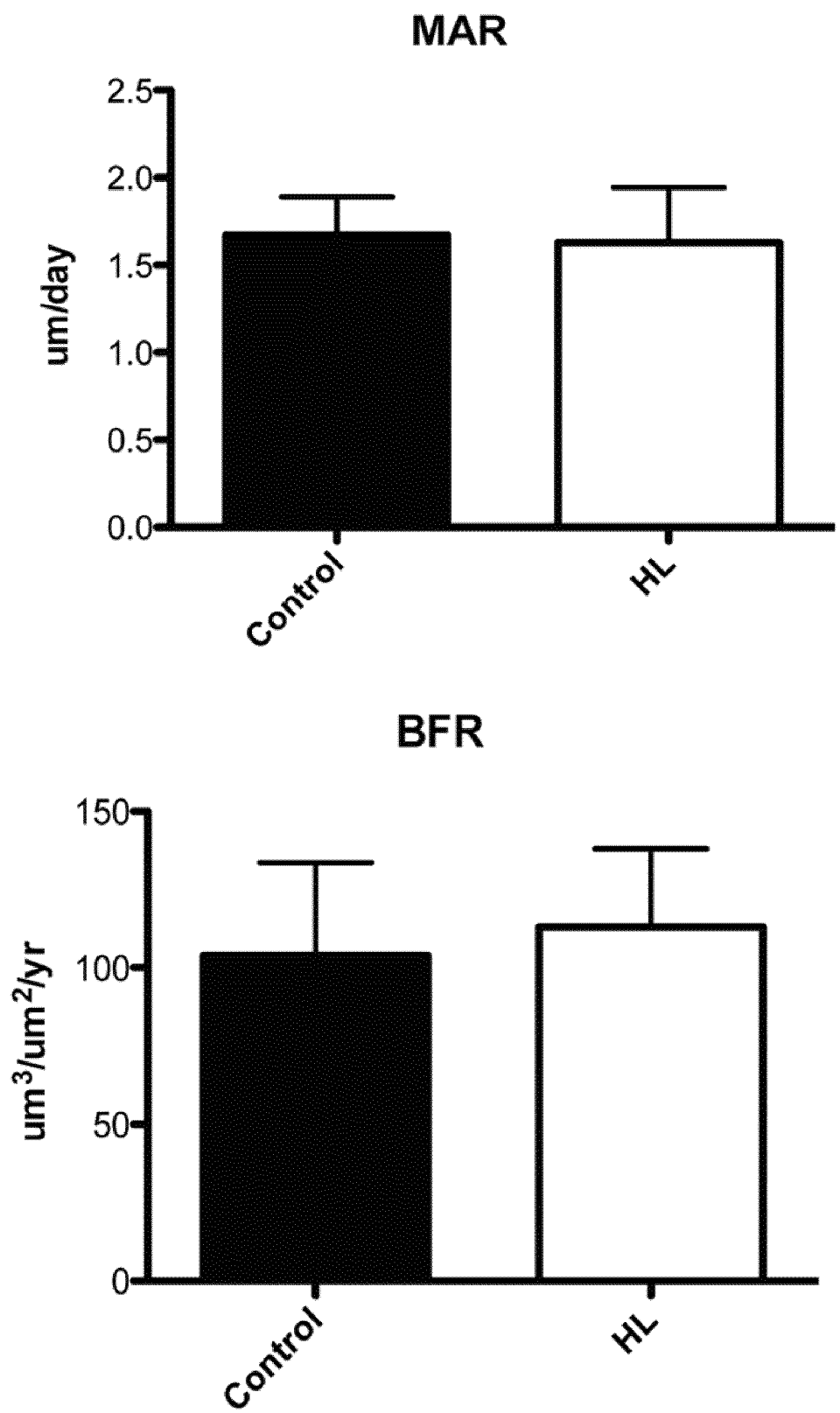
FIG. 15 illustrates Halofuginone does not affect bone formation.

Since Halofuginone inhibits type I collagen synthesis by fibroblasts and other cells, bone formation rates were tested to determine whether the rates are reduced in mice treated with the chemical. Mice were treated daily with HL or vehicle control for 14 days, while Calcein was injected on day 7 and 12, and Mineral Apposition Rates (MAR) and Bone Formation Rates (BFR) were determined. Calcein double labeling of mice treated for two weeks with Halofuginone or PBS control showed equivalent bone formation rates (FIG. 15), indicating Halofuginone does not affect bone formation.

Example 5

This example illustrates that Halofuginone treated mice have less body fat.

Figure 16:
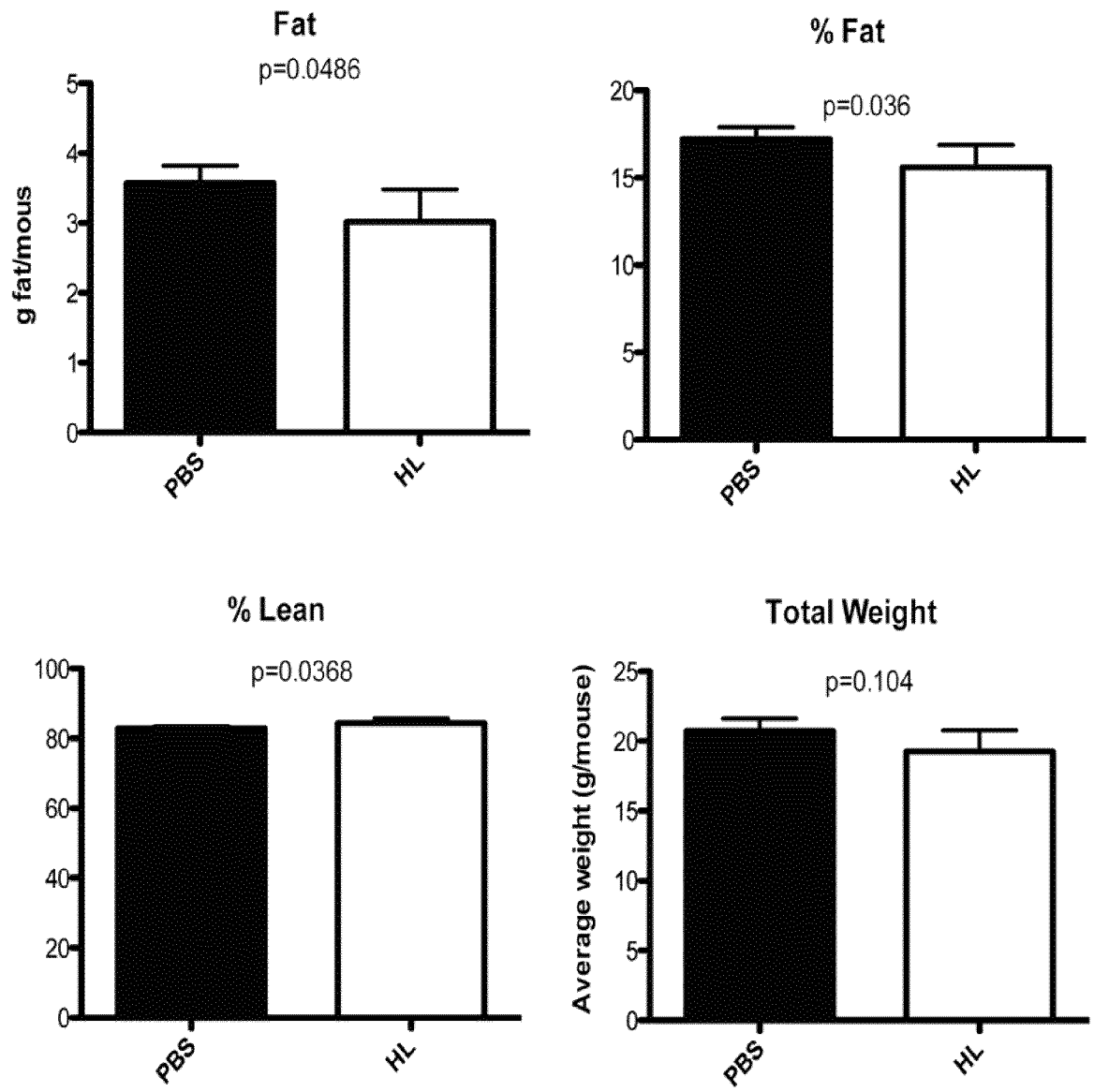
FIG. 16 illustrates body, composition of Halofuginone-treated nice.

IL-17A inhibits adipocyte differentiation from human mesenchymal stem cells (Shin et al., Biochem. Pharmacol., 77(12), 1835-1844, 2009). IL17R−/− mice are heavier and have higher leptin levels, which is a marker of adopocyte mass (Galic et al., Mol. Cell Endocrinol., 316(2), 129-139, 2010; Goswami et al., Eur J Immunol, 39(10), 2831-2839, 2009). Leptin can stimulate IL-17 production (Liu et al., Br. J. Ophthalmol., 92(4), 557-561, 2008), and blood IL-17 levels are increased in obese women (Sumarac-Dumanovic et al., Int. J. Obes. (Lond), 33(1), 151-156, 2009). These data implicate the Th17 axis in adiposity, so magnetic resonance imaging (MRI) was used as a sensitive measure of body composition after 12 weeks of treatment with Halofuginone or vehicle control. Eight week old mice (n=6 mice per group) were treated with Halofuginone or PBS for 12 weeks, after which body content was measured using MRI. Inhibition of IL-17 was expected to lead to increased adiposity, but instead Halofuginone treated mice had significantly less total fat mass, in addition to reduced percent body fat (FIG. 16). Additionally, Halofuginone treatment resulted in a small but statistically significant increase in percent lean mass (FIG. 16).

Example 6

This example further illustrates prevention of bone loss by Halofuginone treatment in estrogen deficient in mice.

The inventors induced estrogen loss osteoporosis by ovariectomy in knockout mice that lack a downstream scaffolding protein in the IL-17 pathway, Act1. Their data indicate that these mice are protected from osteoporosis.

Figure 17:
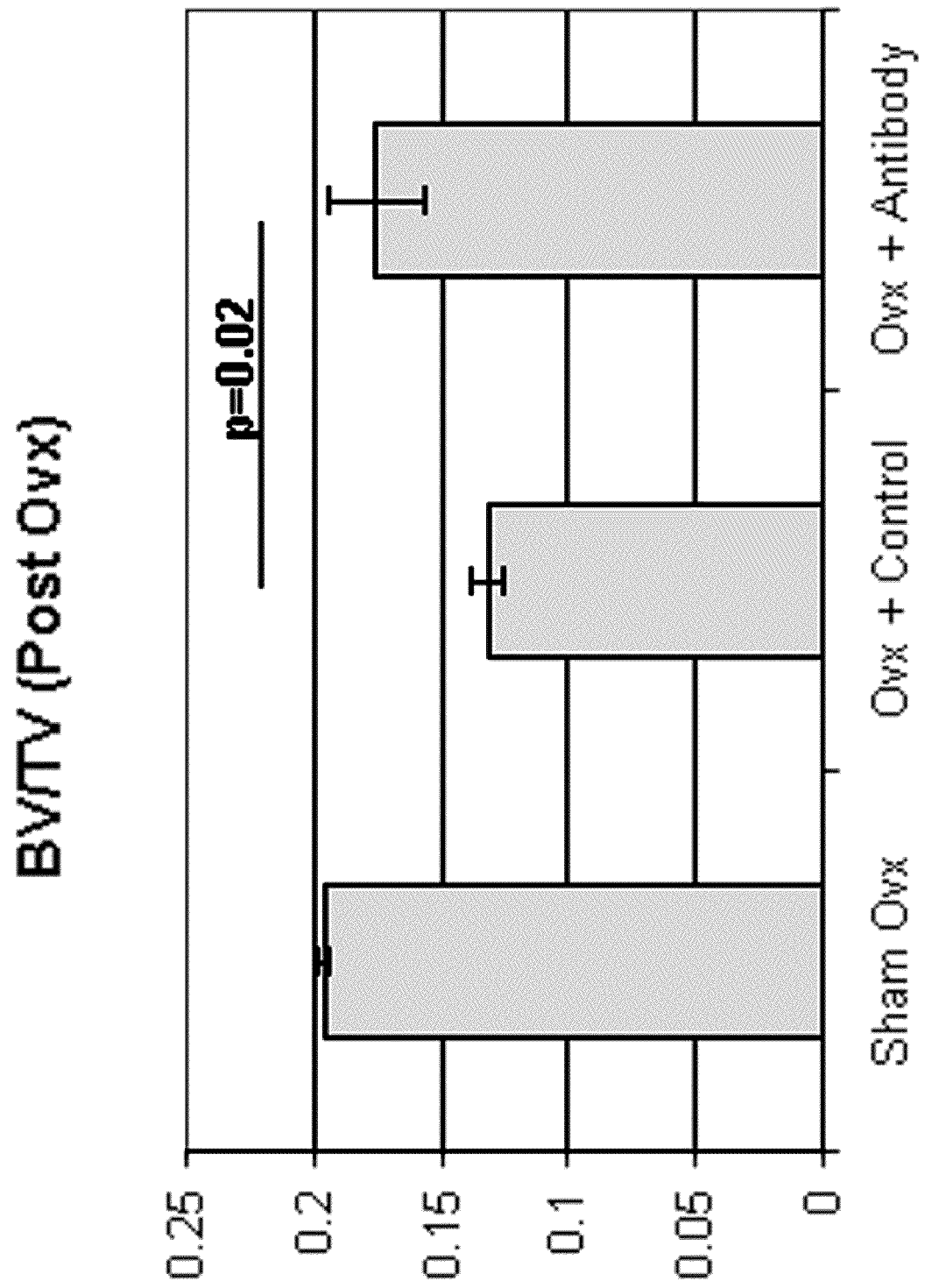
FIG. 17 illustrates an IL-17 blocking antibody protects against bone loss post ovariectomy.

To test whether inhibiting IL-17 has an effect on osteoporosis, the inventors obtained an IL-17 blocking antibody, and gave it to mice IP every 3 days. These mice lost less bone than isotype control treated mice (FIG. 17).

Figure 18:
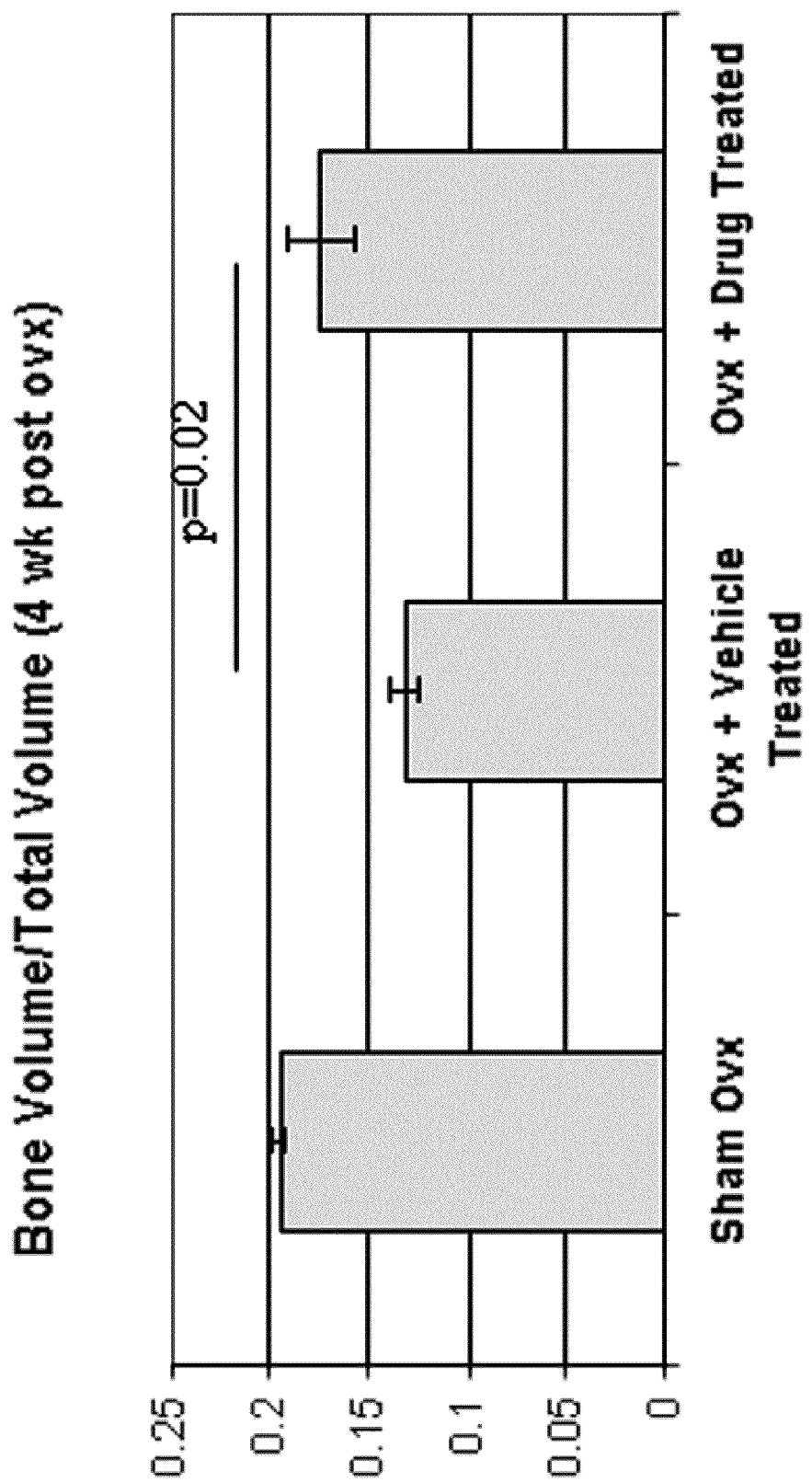
FIG. 18 illustrates Halofuginone-treated mice lose significantly less bone from ovariectomy-induced bone loss at four weeks.
Figure 19:
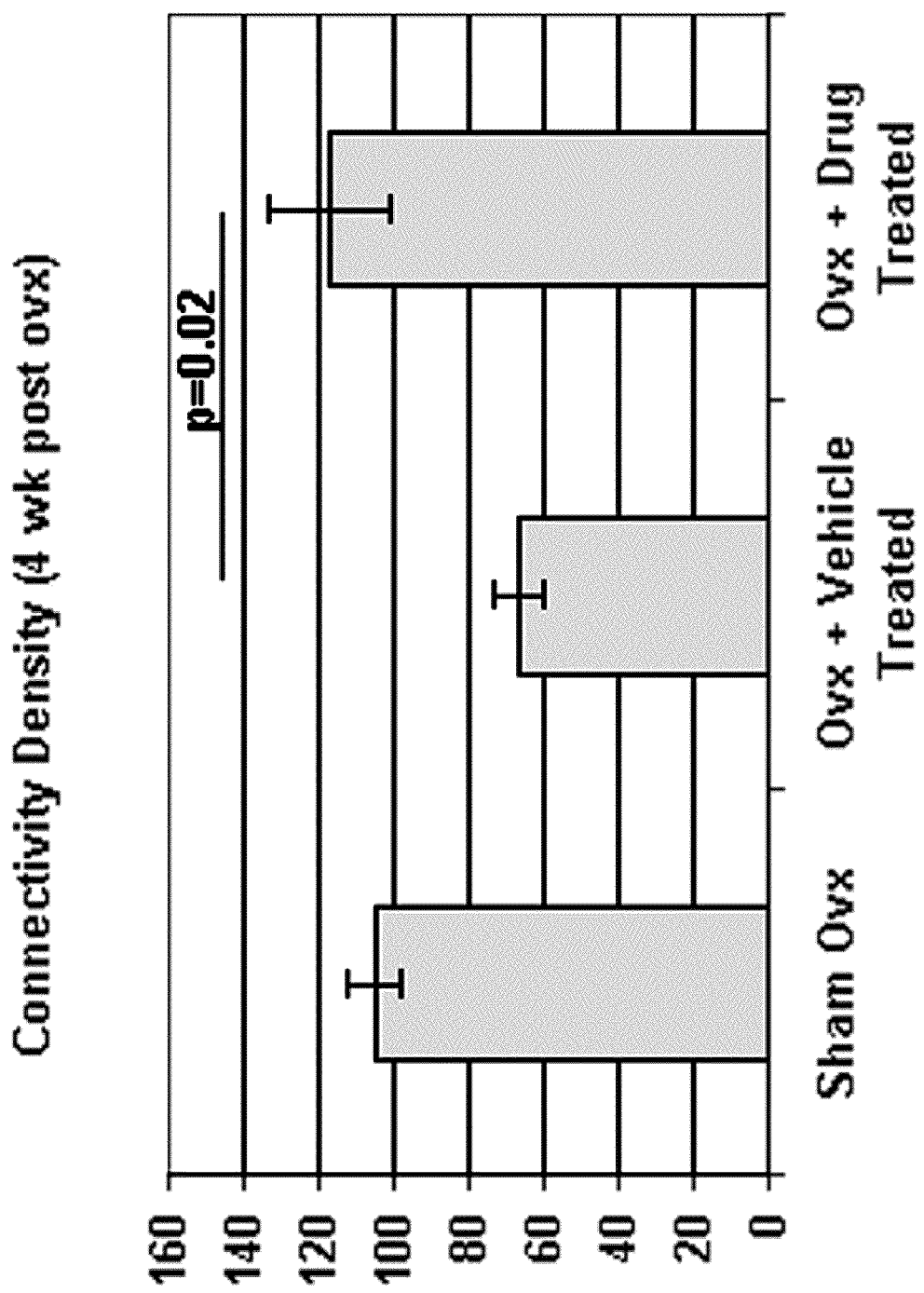
FIG. 19 illustrates that connectivity density was completely protected from ovariectomy-induced bone loss at four weeks.

The inventors injected Halofuginone into mice daily, as was done by Sundrud et al. Four weeks after Ovariectomy, Halofuginone-treated mice lost significantly less bone than PBS injected mice (FIG. 18). Other parameters also indicated that bone was protected. For example, Connectivity Density, which is a measurement of the number of connections made between bony trabeculae, was completely protected (FIG. 19).

Example 7

This example illustrates that Halofuginone-treated mice lose significantly less bone than PBS-treated mice.

Figure 20:
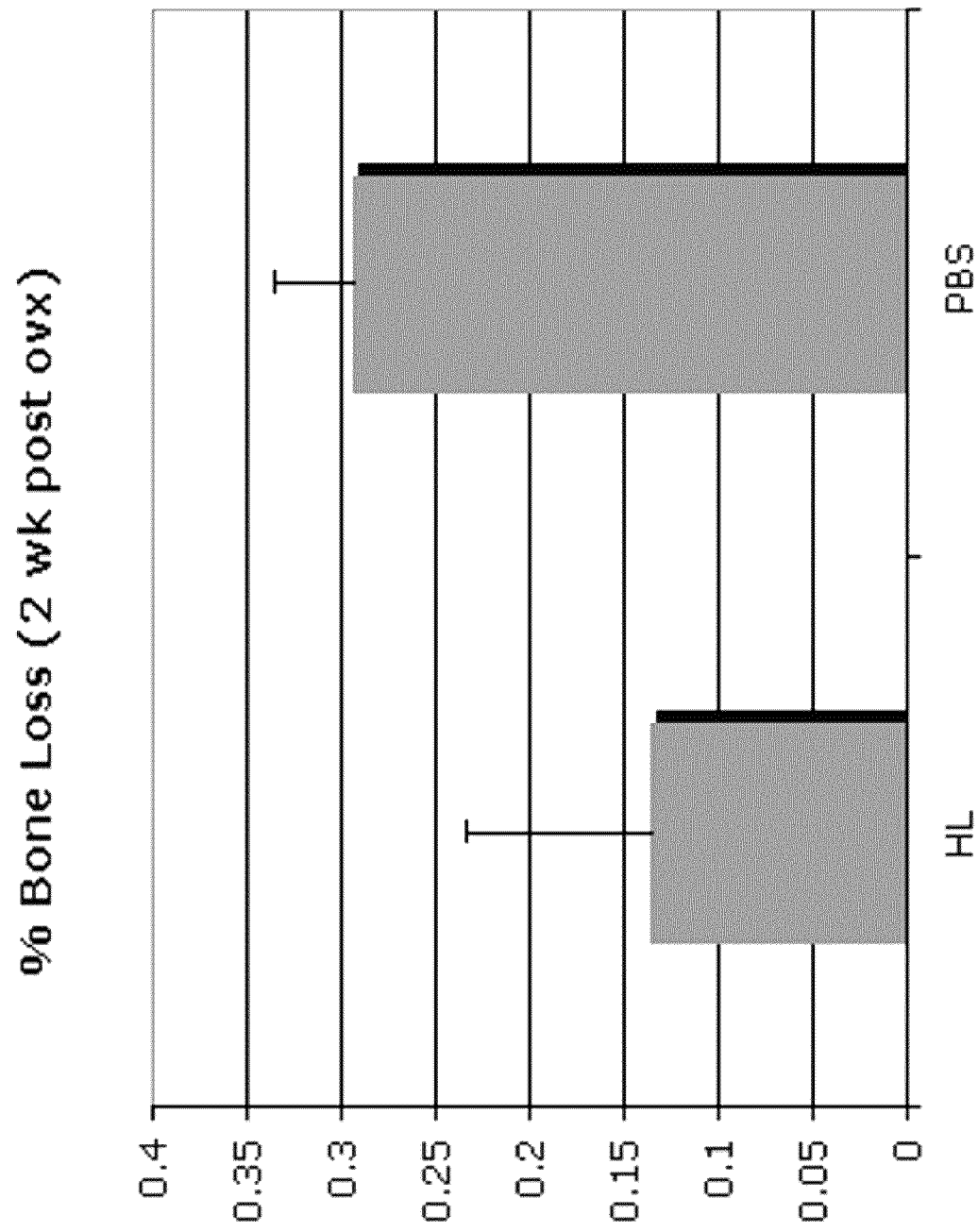
FIG. 20 illustrates Halofuginone-treated mice lose significantly less bone two weeks after ovariectomy.

The inventors measured the bone volume of mice before ovariectomy and two weeks after ovariectomy, and found that each Halofuginone-treated mouse again lost significantly less bone than PBS treated mice (FIG. 20).

Aspects

The present teachings include the following aspects:

1. A method of treating a bone degenerative disease in a subject in need thereof, comprising:
   administering to a subject a therapeutically effective amount of a quinazolinone analogue or a salt or multimer thereof, comprising a radical covalently linked to the nitrogen at the 3 position on the quinazolinone.

2. A method of treating a bone degenerative disease in accordance with aspect 1, wherein the quinazolinone analogue has the structure

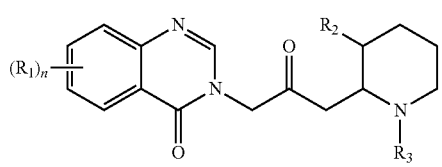

wherein n is 0, 1 or 2; $R_1$ is a hydrogen, a halogen, a nitro, a benzo, a lower alkyl, a phenyl, or a lower alkoxy and is located at one or more of the 6, 7 or 8 positions on the quinazolinone nucleus; $R_2$ is a hydroxyl, an acetoxy, or a lower alkoxy; and $R_3$ is a hydrogen or a lower alkoxycarbonyl; lower alkyl and lower alkoxy radicals can have from 1 to 6 carbons.

3. A method of treating a bone degenerative disease in accordance with aspect 1, wherein the quinazolinone analogue is Halofuginone.

4. A method of treating a bone degenerative disease in accordance with aspect 1, wherein the quinazolinone analogue is febrifugine.

5. A method of treating a bone degenerative disease in accordance with aspect 1, wherein the quinazolinone analogue is selected from the group consisting of (1)

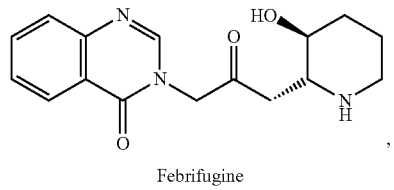

Febrifugine (2)

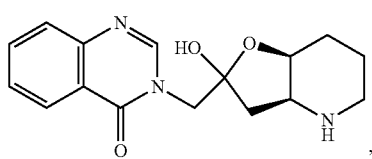

Isofebrifugine (3)

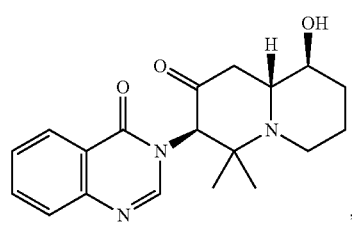

Df-1

(4)

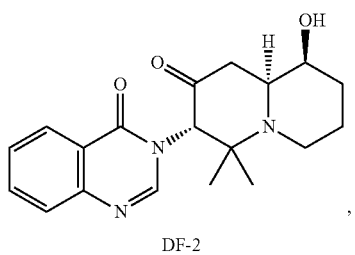

DF-2

(5)

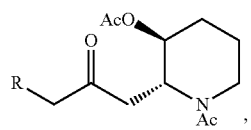

(6)

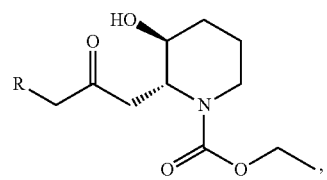

(7)

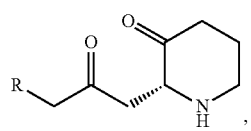

(8)

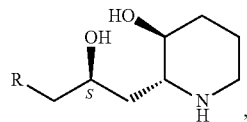

(9)

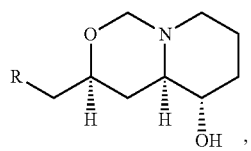

(10)

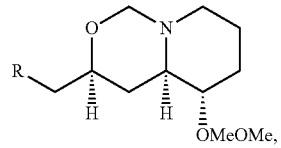

3-{(3S,4aR,5S)-5-Methoxymethyloxy-hexahydropyrido[1,2-c]-[1,3]oxazin-3-ylmethyl}-4(3H)-quinazolinone (11)

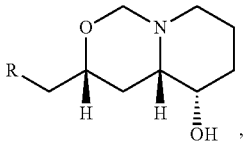

(12)

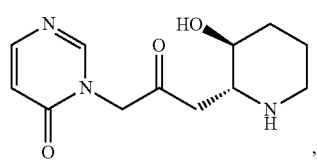

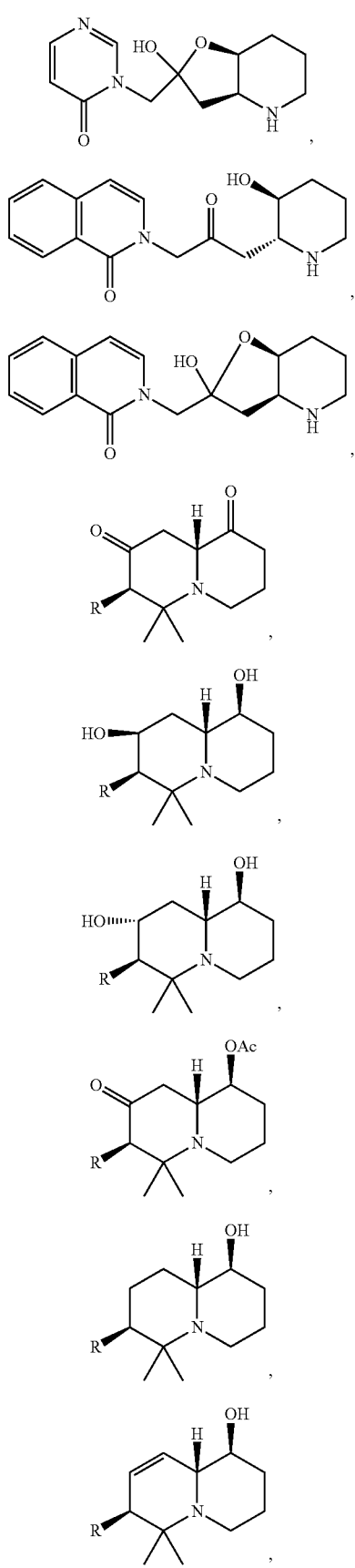
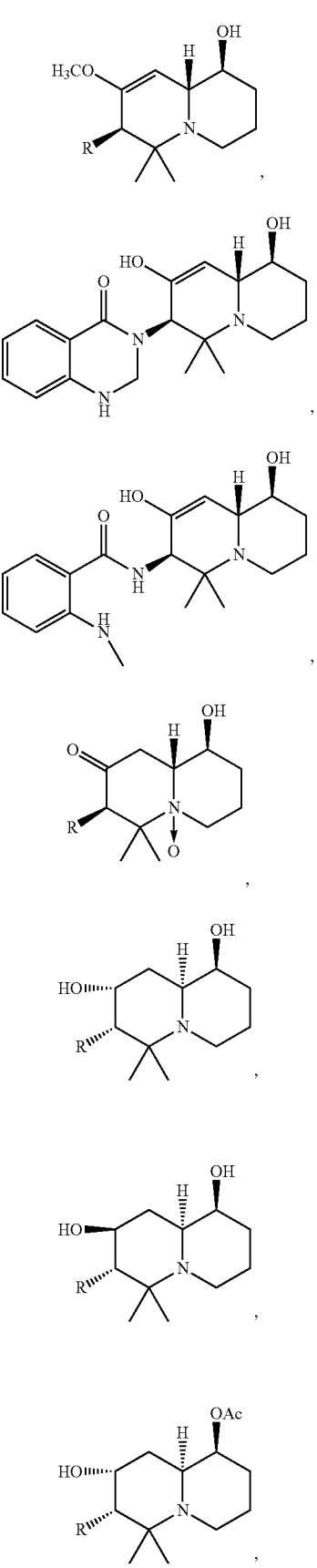

-continued

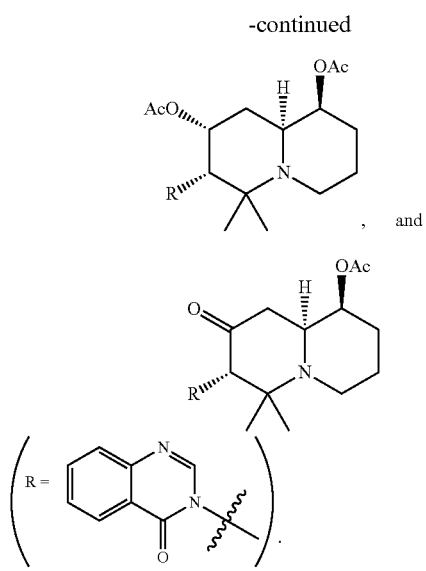

6. A method of treating a bone degenerative disease in accordance with aspect 1, wherein the quinazolinone analogue has an $EC_{50}$ for antimalarial activity less than $10^{-6}$ M.
7. A method of treating a bone degenerative disease in accordance with aspect 1, wherein the quinazolinone analogue has an $EC_{50}$ for antimalarial activity less than $10^{-7}$ M.
8. A method of treating a bone degenerative disease in accordance with aspect 1, wherein the quinazolinone analogue has an $EC_{50}$ for antimalarial activity less than $10^{-8}$ M.
9. A method of treating a bone degenerative disease in accordance with aspect 1, wherein the quinazolinone analogue has an $EC_{50}$ for antimalarial activity less than $10^{-9}$ M.
10. A method of treating a bone degenerative disease in accordance with aspect 1, wherein the quinazolinone analogue is

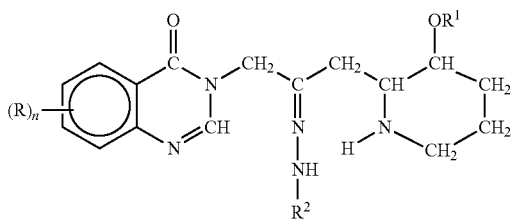

wherein R is an alkyl $C_1$-$C_4$, an alkoxy $C_1$-$C_4$, an alkylthio $C_1$-$C_4$ or a halogen; n is zero, one or two; $R^1$ is a hydrogen atom or an alkyl $C_1$-$C_4$; $R^2$ is a hydrogen atom, an alkyl $C_1$-$C_8$, a cycloalkyl $C_3$-$C_6$ or a phenyl optionally substituted by one or more alkyl $C_1$-$C_4$ or halogen atoms.
11. A method of treating a bone degenerative disease in a subject in need thereof, comprising:
    administering to a subject a therapeutically effective amount of an agent that inhibits signaling through the IL-17 pathway.
12. A method of treating a bone degenerative disease in accordance with aspect 11, wherein the agent that inhibits signaling through the IL-17 pathway is an RNAi.
13. A method of treating a bone degenerative disease in accordance with aspect 11, wherein the agent that inhibits signaling through the IL-17 pathway is an antibody.
14. A method of treating a bone degenerative disease in accordance with any one of aspects 1-13, wherein the bone degenerative disease is selected from the group consisting of osteoporosis an inflammatory osteolysis.
15. A method of treating a bone degenerative disease in accordance with any one of aspects 1-13, wherein the bone degenerative disease is osteoporosis.
16. A method of treating a bone degenerative disease in accordance with any one of aspects 1-15, wherein the subject is a post-menopausal woman.
17. A method of treating a bone degenerative disease in accordance with any one of aspects 1-13, wherein the bone degenerative disease is inflammatory osteolysis.
18. A method of treating a bone degenerative disease in accordance with any one of aspects 1-10, wherein the quinazolinone analogue or a salt or multimer thereof is comprised by a pharmaceutical composition.
19. A composition for treating osteoporosis or other degenerative bone disease, comprising:
    a compound or a pharmaceutically acceptable salt thereof in combination with a pharmaceutically acceptable carrier, said compound having the formula:

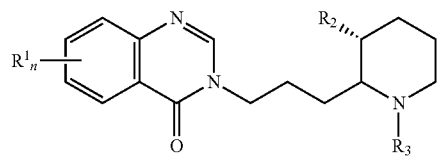

wherein n=0, 1 or 2, $R_1$ is selected from the group consisting of hydrogen, halogen, nitro, benzo, lower alkyl, phenyl and lower alkoxy; $R_2$ is selected from the group consisting of hydroxy, acetoxy and lower alkoxy; and $R_3$ is selected from the group consisting of hydrogen and lower alkenoxy-carbonyl; and
a pharmaceutically acceptable carrier.
20. The composition of aspect 19, wherein said compound is Halofuginone.
21. The composition of aspect 19 wherein said composition is a powder, a granule, a suspension, a solution in water, a non aqueous medium, a sachet, a capsule or a tablet.
22. A method for treating osteoporosis or other degenerative bone disease in a subject in need thereof, comprising administering to said subject a therapeutically effective amount of a pharmaceutical composition comprising as an active ingredient a compound or a pharmaceutically acceptable salt thereof, of

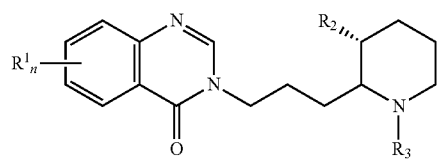

formula wherein n=0, 1 or 2, $R_1$ is selected from the group consisting of hydrogen, halogen, nitro, benzo, lower alkyl, phenyl and lower alkoxy; $R_2$ is selected from the group consisting of hydroxy, acetoxy and lower alkoxy, and $R_3$ is selected from the group consisting of hydrogen and lower alkenoxy-carbonyl.
23. The method of aspect 22, wherein said compound is Halofuginone.
24. The method of aspect 22, wherein said pharmaceutical composition further comprises a pharmaceutically acceptable carrier suitable for administration of the composition orally or parenterally.

25. The method of aspect 24, wherein said pharmaceutical composition comprises a powder, a granule, a solution in water, a suspension in water or non aqueous medium, a solution in water or non aqueous medium, a sachet, a capsule or a tablet.

26. A method for preventing osteoporosis or other degenerative bone disease comprising administering to a subject in need thereof a composition comprising a therapeutically effective amount of compound or a pharmaceutically acceptable salt thereof in a pharmaceutically acceptable carrier, said compound having the

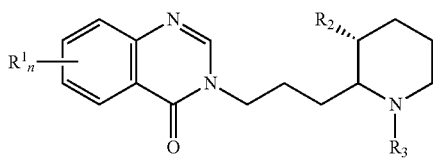

formula wherein n=0, 1 or 2, $R_1$ is selected from the group consisting of hydrogen, halogen, nitro, benzo, lower alkyl, phenyl and lower alkoxy; $R_2$ is selected from the group consisting of hydroxy, acetoxy and lower alkoxy; and $R_3$ is selected from the group consisting of hydrogen and lower alkenoxy-carbonylf.

27. The method of aspect 26, wherein said compound is Halofuginone.

28. The method of aspect 26, wherein the pharmaceutically acceptable carrier is suitable for administration orally or parenterally.

29. The method of aspect 26, wherein said pharmaceutically acceptable carrier comprises a powder, a granule, a solution in water, a suspension in water or non aqueous medium, a solution in water or non aqueous medium, a sachet, a capsule or a tablet.

All publications, patent applications, patents, and other references cited herein are incorporated by reference, each in its entirety.

What is claimed is:

1. A method of treating osteoporosis in a subject in need thereof, comprising:
   administering to a subject a therapeutically effective amount of a quinazolinone analogue, wherein the quinazolinone analogue is Halofuginone having the formula

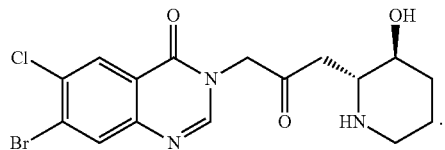 [SMILES: O=C(C[C@H]1NCCC[C@@H]1O)Cn1cnc2cc(Br)c(Cl)cc2c1=O]

2. A method of treating osteoporosis in accordance with claim 1, wherein the subject is a post-menopausal woman.

3. A method of treating osteoporosis in accordance with claim 1, wherein the halofuginone is comprised by a pharmaceutical composition.

* * * * *